US011406922B2

(12) United States Patent
Kirschman

(10) Patent No.: US 11,406,922 B2
(45) Date of Patent: Aug. 9, 2022

(54) SECURITY SYSTEM FOR FLUID FILTRATION DEVICE

(71) Applicant: David Louis Kirschman, Dayton, OH (US)

(72) Inventor: David Louis Kirschman, Dayton, OH (US)

(73) Assignee: Aerobiotix, LLC, Miamisburg, OH (US)

( * ) Notice: Subject to any disclaimer, the term of this patent is extended or adjusted under 35 U.S.C. 154(b) by 7 days.

(21) Appl. No.: 16/419,410

(22) Filed: May 22, 2019

(65) Prior Publication Data

US 2020/0047094 A1 Feb. 13, 2020

Related U.S. Application Data

(60) Provisional application No. 62/716,435, filed on Aug. 9, 2018.

(51) Int. Cl.
*B01D 35/143* (2006.01)

(52) U.S. Cl.
CPC ...... *B01D 35/1435* (2013.01); *B01D 2201/52* (2013.01); *B01D 2201/54* (2013.01)

(58) Field of Classification Search
CPC .............. B01D 35/143; B01D 35/1435; B01D 2201/54; B01D 2201/52; B01D 27/101; B01D 27/10; C02F 1/00; C02F 1/008; C02F 9/00; C02F 2307/10; G16H 10/40; G16H 40/60; G06K 7/00; G06K 7/0008; F25C 5/00

USPC .......................................................... 210/85
See application file for complete search history.

(56) References Cited

U.S. PATENT DOCUMENTS

| | | |
|---|---|---|
| 4,585,164 A | 4/1986 | Butkovich et al. |
| 4,786,295 A | 11/1988 | Newman et al. |
| 5,036,698 A | 8/1991 | Conti |
| 5,635,403 A | 6/1997 | Bailey |
| 5,668,535 A | 9/1997 | Hendrix et al. |
| 5,674,381 A | 10/1997 | Den Dekker |
| 5,810,908 A | 9/1998 | Gray et al. |
| 5,862,737 A | 1/1999 | Chiu et al. |
| 6,040,777 A | 3/2000 | Ammann et al. |
| 6,190,442 B1 | 2/2001 | Redner |
| 6,203,590 B1 | 3/2001 | Byrd et al. |
| 6,385,510 B1 | 5/2002 | Hoog et al. |
| 6,391,102 B1 | 5/2002 | Bodden et al. |
| 6,448,896 B1 | 9/2002 | Bankus et al. |
| 6,466,132 B1 | 10/2002 | Caronna et al. |
| 7,594,960 B2 | 9/2009 | Johansson |
| 7,638,042 B2 | 12/2009 | Astle et al. |
| 7,686,872 B2 | 3/2010 | Kang |
| 7,713,339 B2 | 5/2010 | Johansson |

(Continued)

FOREIGN PATENT DOCUMENTS

| | | | |
|---|---|---|---|
| EP | 3138817 A1 * | 3/2017 | ............. B01D 35/02 |
| EP | 3138817 A1 | 3/2017 | |

*Primary Examiner* — Akash K Varma
(74) *Attorney, Agent, or Firm* — Jacox, Meckstroth & Jenkins

(57) ABSTRACT

A security system for a fluid filtration device and, more particularly, a security system that is adapted to pair a filter with a fluid filtration device, log an effectiveness of each individually serialized filter, prevent re-usage of a filter in more than one filtration device and prevent usage of a filter for greater than its preprogrammed lifespan.

53 Claims, 7 Drawing Sheets

(56) References Cited

U.S. PATENT DOCUMENTS

| | | |
|---|---|---|
| 8,701,980 B2 | 4/2014 | Calio et al. |
| 9,311,807 B2 | 4/2016 | Schultz et al. |
| 9,366,448 B2 | 6/2016 | Dean-Hendricks et al. |
| 9,409,114 B2 | 8/2016 | Sullivan |
| 9,448,144 B2 | 9/2016 | Calio, Jr. et al. |
| 9,517,428 B2 | 12/2016 | Francis et al. |
| 9,658,140 B2 | 5/2017 | Calio et al. |
| 9,783,430 B2 | 10/2017 | Rice |
| 2003/0070544 A1 | 4/2003 | Mulvaney et al. |
| 2006/0060512 A1* | 3/2006 | Astle .................. B01D 29/606 210/85 |
| 2007/0013534 A1 | 1/2007 | DiMaggio |
| 2010/0096302 A1 | 4/2010 | Astle et al. |
| 2011/0185895 A1 | 8/2011 | Freen |
| 2012/0318073 A1 | 12/2012 | Zavodny et al. |
| 2012/0318135 A1 | 12/2012 | Hoglund et al. |
| 2012/0319851 A1 | 12/2012 | Hoglund et al. |
| 2014/0266755 A1 | 9/2014 | Arensmeier et al. |
| 2014/0283682 A1 | 9/2014 | Hamann et al. |
| 2016/0046502 A1* | 2/2016 | Rice ....................... C02F 1/003 210/85 |
| 2017/0050130 A1 | 2/2017 | Bippus et al. |

* cited by examiner ically to provisional U.S. Application Ser. No. 62/716,435, filed Aug. 9, 2018, to which Applicant claims the benefit of the earlier filing date. This provisional application is incorporated herein by reference and made a part hereof.

SECURITY SYSTEM FOR FLUID FILTRATION DEVICE

CROSS-REFERENCE TO RELATED APPLICATION

The present application claims priority to provisional U.S. Application Ser. No. 62/716,435, filed Aug. 9, 2018, to which Applicant claims the benefit of the earlier filing date. This provisional application is incorporated herein by reference and made a part hereof.

BACKGROUND OF THE INVENTION

1. Field of the Invention

This invention relates to a security system for a fluid filtration device and, more particularly, a security system that is adapted to pair a filter with a fluid filtration device, log an effectiveness of each individually serialized filter, prevent re-usage of a filter in more than one filtration device and prevent usage of a filter for greater than its preprogrammed lifespan.

2. Description of the Related Art

Proper fluid filtration is important in hospital settings to prevent environmental transmission of infectious agents, such as those which occur in air and water. Recently, a new generation of mobile air filtration devices has been developed for hospital usage, exemplified in U.S. Pat. Nos. 9,433,693 and 9,764,054. These devices have proven to be effective in reducing environmental infectious agents and multiple units can be deployed within areas of need in the hospital setting. However, placement of such fluid filtration devices in health care settings presents a set of unique challenges which requires new methods to maximize safety and effectiveness of the filtration device.

What is needed is a digitally-based data security system located in both a filter and a parent fluid handling device capable of reading, writing, and storage of data to achieve the security objectives, including prevention of filter re-use, tampering, or over-use.

SUMMARY OF THE INVENTION

One object of the invention is to provide a security system for use in a fluid filtration device.

Another object of the invention is to provide a filtration device having a security system that logs an effectiveness of each individualized and serialized filter.

Another object of the invention is to provide a filtration device having a security system adapted to prevent re-usage of a filter element in more than one filtration device.

Still another object of the invention is to provide a security system for use in a filtration device that prevents usage of a filter beyond its preprogrammed lifespan.

Yet another object of the invention is to provide a fluid filtration device that is adapted to collect parameter information regarding the usage and effectiveness of a filter that is situated in the device.

Another object of the invention is to provide a digitally-based data security system on a filter that communicates and cooperates with an electronic means or communication on the fluid filtration device.

Yet another object of the invention is to provide a process or procedure for controlling an operation of a fluid filtration device and that facilitates improving the overall effectiveness of the device when removing contaminants, airborne bacteria and/or other pathogens in the fluid passing through the device.

Still another object of the invention is to provide a security system for tracking filter usage.

Another object of the invention is to provide a security system that is adapted for logging of the effectiveness of each individually serialized filter cartridge to determine if filter adulteration has taken place, to prevent re-usage of a filter element in more than one filtration device, and to prevent filter use for greater than its preprogrammed lifespan.

In one aspect, one embodiment of the invention comprises a fluid filtration security system comprising a fluid handler having a housing having at least one filter receiving area for receiving at least one filter, the fluid handler having a fluid handler identification code associated therewith and the at least one filter having at least one filter identification code associated therewith, and a fluid treatment processor for generating at least one pairing identification code in response to the fluid handler identification code and the at least one filter identification code, wherein the fluid treatment processor controls an operation of the fluid handler and at least one of logs a filter effectiveness associated with the at least one filter, prevents a re-usage of the at least one filter if the at least one filter fails at least one predetermined filter usage criteria, or prevents use of the at least one filter if a usage time of the at least one filter exceeds a predetermined usage time or if the fluid handler identification code of the at least one pairing identification code does not match the fluid handler identification code for the fluid handler.

In another aspect, one embodiment of the invention comprises a security method for use in a filtration device, the method comprising the following steps: programming a fluid handler with a fluid handler identification code unique to the fluid handler, initiating transference of the fluid handler identification code to at least one filter when the at least one filter is received in a filter receiving area of the fluid handler, the fluid handler identification code resulting in an exclusive pairing of the at least one filter to the fluid handler, such that the at least one filter cannot be used in any other fluid handler other than the fluid handler which first wrote the fluid handler identification code.

In another aspect, one embodiment of the invention comprises a security method for a fluid handler, the security method comprising the steps of: bidirectionally transferring at least one filter identification code associated with at least one filter and a fluid handler identification code for the fluid handler to the fluid handler and the at least one filter, respectively, in order to exclusively pair the at least one filter to the fluid handler, and initiating a timer or timing means to clock a filter usage time for the at least one filter after it is received by the fluid handler, interrupting or preventing the fluid handler from operating if the filter usage time exceeds a predetermined maximum usage time for the at least one filter.

In yet another aspect, one embodiment of the invention comprises a disinfection system for disinfecting fluid passing through the disinfection system, the disinfection system comprising a fluid handler comprising a housing having at least one filter receiving area for receiving at least one filter for filtering air passing through the disinfection system, a filter tracking system adapted to perform at least one of the following: tracking at least one of a filter effectiveness associated with the at least one filter, preventing a re-usage of the at least one filter if the at least one filter fails at least one predetermined filter usage criteria, preventing use of the at least one filter if a usage time of the at least one filter has expired, or preventing the fluid handler from operating if a verification code associated with the at least one filter is not verified.

In another aspect, one embodiment of the invention comprises a security system for a fluid filtration device comprising electronic means for transferring data bidirectionally between a changeable filter component and a fluid handler, at least one of the filter and the handler incorporating preprogrammed unique internal identification codes.

In still another aspect, one embodiment of the invention comprises a security system for a filtration device comprising a database which receives and encodes a unique identification code originating in an individual filter and pairs the code with system performance data, the identification code and the performance data allowing a user to evaluate the performance of the individual filter, the performance data consisting of fluid quality, fluid flow, power draw, timing, or other parameters determining system integrity.

In another aspect, one embodiment of the invention comprises a method for programming a security system for a filtration device, the method comprising the steps of: programming a fluid handler with an identification code unique to the fluid handler, installing the filter in the fluid handler, initiating transference of the identification code to the filter, and exclusively pairing the filter to the fluid handler such that the filter cannot be used in any other fluid handler than the one to which it was paired.

In another aspect, one embodiment of the invention comprises a method for programming a security system for a filtration device, the method comprising the steps of installing a fluid filter in a fluid handler, bidirectionally transferring unique identification codes between the handler and the filter resulting in an exclusive pairing of the filter to the fluid handler, and initiating a timing means to clock the usage time of that filter in that handler.

This invention, including all embodiments shown and described herein, could be used alone or together and/or in combination with one or more of the features covered by one or more of the following list of features:

The fluid filtration security system wherein the fluid treatment processor programs the at least one filter with the fluid handler identification code when the at least one filter is received in the at least one filter receiving area and generates a filter-handler pairing code in response thereto; the fluid treatment processor subsequently preventing or locking out the fluid handler from operating if the at least one filter identification code of at least one filter that is received in the at least one filter receiving area of the fluid handler does not match the fluid handler identification code for the fluid handler.

The fluid filtration security system wherein the fluid handler comprises a reader-writer associated with the at least one filter receiving area and the at least one filter comprises at least one of a filter processor or a memory on the at least one filter, a fluid treatment processor communicating the handler identification code to the at least one filter processor or memory when the at least one filter is received in the at least one filter receiving area; the reader-writer also being adapted to read at least one of the filter identification code, fluid handler identification code or the at least one pairing code to permit the fluid treatment processor to control an operation of the fluid handler in response thereto.

The fluid filtration security system wherein the at least one filter has an associated predetermined useful life, the fluid treatment processor preventing or interrupting an operation of the fluid handler if an actual use life of the at least one filter exceeds the predetermined usage time.

The fluid filtration security system wherein the fluid treatment processor stores the predetermined usage time into a database when the at least one filter is inserted in the at least one filter receiving area.

The fluid filtration security system wherein the reader-writer reads the at least one filter identification code and the fluid treatment processor receives the at least one filter identification code and combines it with the fluid handler identification code and creates the at least one pairing identification code in response thereto, the fluid treatment processor preventing the fluid handler from operation if at least one of the following conditions occurs: the fluid handler identification code of the at least one pairing identification code does not match the fluid handler identification code for the fluid handler in which the at least one filter is received; or a predetermined usage for the at least one filter exceeds a predetermined usage time.

The fluid filtration security system wherein the fluid filtration security system comprises verification means for preventing the at least one filter from being used in different fluid handlers.

The fluid filtration security system wherein the verification means comprises the fluid treatment processor that causes the reader-writer to write or store the fluid handler identification code onto a data receiver located on the at least one filter, the fluid handler also creating a pairing identification code by combining or processing the fluid handler identification code with the at least one filter identification code which the fluid handler stores in memory; the fluid treatment processor comparing the fluid handler identification code stored on each of the at least one filter that is received in the at least one filter receiving area with the fluid handler's identification code and interrupting or locking the fluid handler from operation if they are different.

The fluid filtration security system wherein the fluid treatment processor permanently causes the fluid handler identification code to be stored or written to the data receiver of the at least one filter.

The fluid filtration security system wherein upon installation of the at least one filter into the at least one filter receiving area, the fluid treatment processor initiates a timer or clock that clocks a filter usage time for the at least one filter, the fluid treatment processor interrupting or preventing the fluid handler from running if the filter usage time exceeds a predetermined filter running time.

The fluid filtration security system wherein the fluid treatment processor causes the filter usage time to be stored in memory and associated with the pairing identification code so that the at least one filter can be removed or re-installed without loss of any remaining the filter usage time.

The fluid filtration security system wherein the fluid handler comprises a database or lookup table for storing expiration data by at least one filter identification code for any the at least one filter having an actual filter usage time that exceeds a predetermined filter running time, the fluid treatment processor recording an expired filter indicator in the database or lookup table and interrupting or preventing the fluid handler from operating if the fluid treatment processor determines that the at least one filter that is received in the at least one filter receiving area has expired.

The fluid filtration security system wherein the fluid treatment processor tracks an actual usage time for the at least one filter, and associates such actual usage time with the at least one pairing identification code; the fluid treatment processor preventing or terminating operation of the fluid handler if the actual usage time exceeds the predetermined usage time.

The fluid filtration security system wherein the fluid treatment processor controls an operation of the fluid handler in response to the at least one pairing identification code in order to log at least one filtration effect.

The fluid filtration security system wherein the fluid treatment processor receives the at least one filter identification code and processes it with the fluid handler identification code and creates a pairing code in response thereto.

The fluid filtration security system wherein the fluid handler comprises a database or lookup table for storing expiration data or predetermined filter useful life data for any of the at least one filter having an actual filter usage time that exceeds a predetermined filter useful life, the fluid treatment processor recording an expired filter indicator in the database or lookup table and interrupting or preventing the fluid handler from operating if the fluid treatment processor determines that the at least one filter that is received in the at least one filter receiving area has expired.

The fluid filtration security system wherein the fluid treatment processor tracks the actual filter usage time for the at least one filter when it is situated in the at least one filter receiving area and associates the actual filter usage time with at least one of the at least one pairing identification code for the at least one filter or the filter identification code and stores the actual filter usage time in the database or lookup table.

The fluid filtration security system wherein the fluid filtration security system generates and maintains a database of expired filter identification codes for each of the at least one filter that has an expired useful life, each of the expired filter identification codes being generated when a difference between an actual filter usage time exceeds a predetermined filter maximum running time, the fluid treatment processor interrupting or preventing the fluid handler from operating in response to the expired filter identification code associated with at least one filter that is received or stored in the at least one filter receiving area that has expired.

The fluid filtration security system wherein fluid filtration security system comprises at least one sensor for sensing and logging into a database at least one filter usage effectiveness for each of the at least one filter that is received in the at least one filter receiving area, the fluid treatment processor interrupting or preventing the fluid handler from operating if the fluid treatment processor determines that the at least one filter effectiveness is below a predetermined threshold.

The fluid filtration security system wherein the fluid handler transmits and writes an expiration code onto the at least one filter if the at least one filter is expired, the fluid handler checking for an expiration code for any of the at least one filter that is receiving in the at least one filter receiving area, the fluid treatment processor interrupting or preventing the fluid handler from operating if any of the at least one filter that is inserted into the at least one filter receiving area has expired.

The fluid filtration security system wherein each of the at least one filter has an encoded filter maximum running time, the fluid treatment processor interrupting or preventing the fluid handler from operating if an actual running time for the at least one filter exceeds the encoded filter maximum running time.

The fluid filtration security system wherein the fluid handler is adapted to receive a plurality of filters, each having a different encoded filter running time or useful life; the fluid treatment processor enacting expiration timing specific to each of the plurality of filters in response to the encoded filter running time or useful life.

The fluid filtration security system wherein the fluid handler comprises a database that receives and encodes a unique filter identification code for the at least one filter and pairs the unique filter identification code with filter performance data for the at least one filter, the filter performance data permitting a user to evaluate a performance of the at least one filter, the filter performance data comprising at least one of fluid quality, fluid flow, power draw for the fluid handler, timing or at least one of other system integrity parameters for determining system integrity.

The fluid filtration security system wherein the fluid filtration security system comprises communication means for permitting communication between the at least one filter and the fluid handler, the communication means comprising at least one of radio frequency transmission, direct electrical communication, optical signaling, infrared signaling or via a digital network.

The fluid filtration security system wherein each of the at least one filter and the fluid handler comprise logic means comprising input, output and memory means.

The fluid filtration security system wherein data associated with at least one of the at least one filter or the fluid handler is encrypted before at least one of encoding or transmission.

The security method for a fluid handler wherein the security method further comprises the steps of: causing reciprocal communication between the at least one filter and the fluid handler such that the at least one filter receives the fluid handler identification code and the fluid handler receives the filter identification code and a filter time code associated with a predetermined filter time; subtracting an actual operating time for the at least one filter from the filter time code generally representing an actual time of usage for the at least one filter; retaining the filter identification code and its associated filter time code in memory, even if the at least one filter is removed and re-installed.

The security method for a fluid handler wherein the security method further comprises the step of: interrupting or ceasing operation of the fluid handler if the actual operating time exceeds the time associated with the filter time code.

The security method for a fluid handler wherein the security method further comprises the step of: annulling the filter time code on the at least one filter if the actual operating time exceeds the time associated with the filter time code and entering the at least one filter identification code into an expired filter database; checking the filter identification code for any filter inserted into the fluid handler against the expired filter database, and if an annulled filter time code is present in the expired filter database, then preventing the fluid handler from operating.

The security method for a fluid handler wherein the security method further comprises the step of: recording performance data associated with the at least one filter into a performance database having performance data for a plurality of filters; the performance database comprising filter-specific performance data in association with each of the plurality of filters; using such performance data to determine a performance and integrity of at least one of the plurality of filters that were used in the fluid handler.

The disinfection system wherein the disinfection system comprises a fluid treatment processor and associated database, the fluid treatment processor causing a fluid handler identification code to be permanently written to the at least one filter when the at least one filter is inserted into the at least one filter receiving area.

The disinfection system wherein the at least one filter comprises a filter identification code, the fluid handler comprising a reader/writer device adapted to read the filter identification code for storage in the fluid handler and also for generating a pairing code in response thereto, the pairing code being used to generate the verification code.

The disinfection system wherein the pairing code comprises a combination of the fluid handler identification code and the filter identification code; the fluid treatment processor preventing the fluid handler from operating when the at least one filter is inserted into the fluid handler and the reader/writer device reads a code associated with the at least one filter that does not match the pairing code.

The disinfection system wherein the at least one filter comprises a filter identification code and a maximum filter time generally representing a maximum time the at least one filter can be used; the fluid handler comprising a reader/writer device adapted to read the filter identification code and the maximum filter time and record them in a fluid handler memory; the fluid treatment processor monitoring an actual time of usage for the at least one filter and preventing the fluid handler from operating when the actual time of usage is greater than the maximum filter time.

The disinfection system wherein the at least one filter comprises data storage for storing data associated with the at least one filter, the data comprising a maximum filter time, a filter identification code, and a fluid handler identification code.

The disinfection system wherein the fluid treatment processor reads the filter identification code when the at least one filter is inserted into the at least one filter receiving area of the fluid handler and combines the filter identification code with the fluid handler identification code to create a pairing code, the fluid treatment processor using the pairing code to control an operation of the fluid handler.

The disinfection system wherein the fluid treatment processor prevents the fluid handler from operating if the fluid handler identification code of the pairing code is different from the fluid handler identification code for the fluid handler or if the at least one filter identification code is not verified against a database by the fluid treatment processor.

The security system wherein upon initial installation of the filter to the handler, the fluid handler transfers a handler identification code identifying the handler from the handler to the filter, the filter then recording the handler identification code, the fluid handler further comprising receiving means to receive a filter identification code from the filter, the fluid handler comparing the handler identification code originating in or received by the filter to a filter handler identification code, the security system providing lockout means to prevent the handler from functioning if the handler identification code received from filter does not match its internal handler identification code, thereby preventing the use of an individual filter in more than one handler.

The security system which upon installation of the filter to the handler and thereafter, initiates timing codes clocking the filter usage time, paired or associated with the filter identification code, the security system providing limit means to prevent handler from functioning if a predetermined filter running time has elapsed, the security system further allowing for individual filter removal and re-installation, without loss of timing data.

The security system providing limit means to prevent the handler from functioning if a filter usage time has expired, the security system further encoding and retaining a database of expired filter identification codes, thus preventing the re-use of an expired filter.

The security system wherein all new filters, when installed in the fluid handler communicate a filter identification code to the handler, the handler checking the filter identification code against a database of expired codes, the fluid handler preventing operation if a new filter identification code for a new filter is present in the database.

The security system wherein the handler transmits, and the filter receives and records, an expiration code upon expiration of the filter, the expiration code being used to prevent the filter from being used in response to the expiration code.

The security system wherein the predetermined filter running time is encoded in the filter, the security system allowing for different filter types with varying predetermined filter running times to be received by handler and handler enacting expiration timing specific for the filter type.

The security system wherein communication means between the filter and the handler are via radiofrequency transmission, direct electrical contact, optical signaling, infrared signal, or via digital network.

The security system wherein the filter and handler comprise logic means consisting of input, output, and memory means.

The security system wherein encoding and/or transmission of handler and/or filter data is encrypted.

These and other objects and advantages of the invention will be apparent from the following description, the accompanying drawings and the appended claims.

BRIEF DESCRIPTION OF THE ACCOMPANYING DRAWINGS

Figure 5:
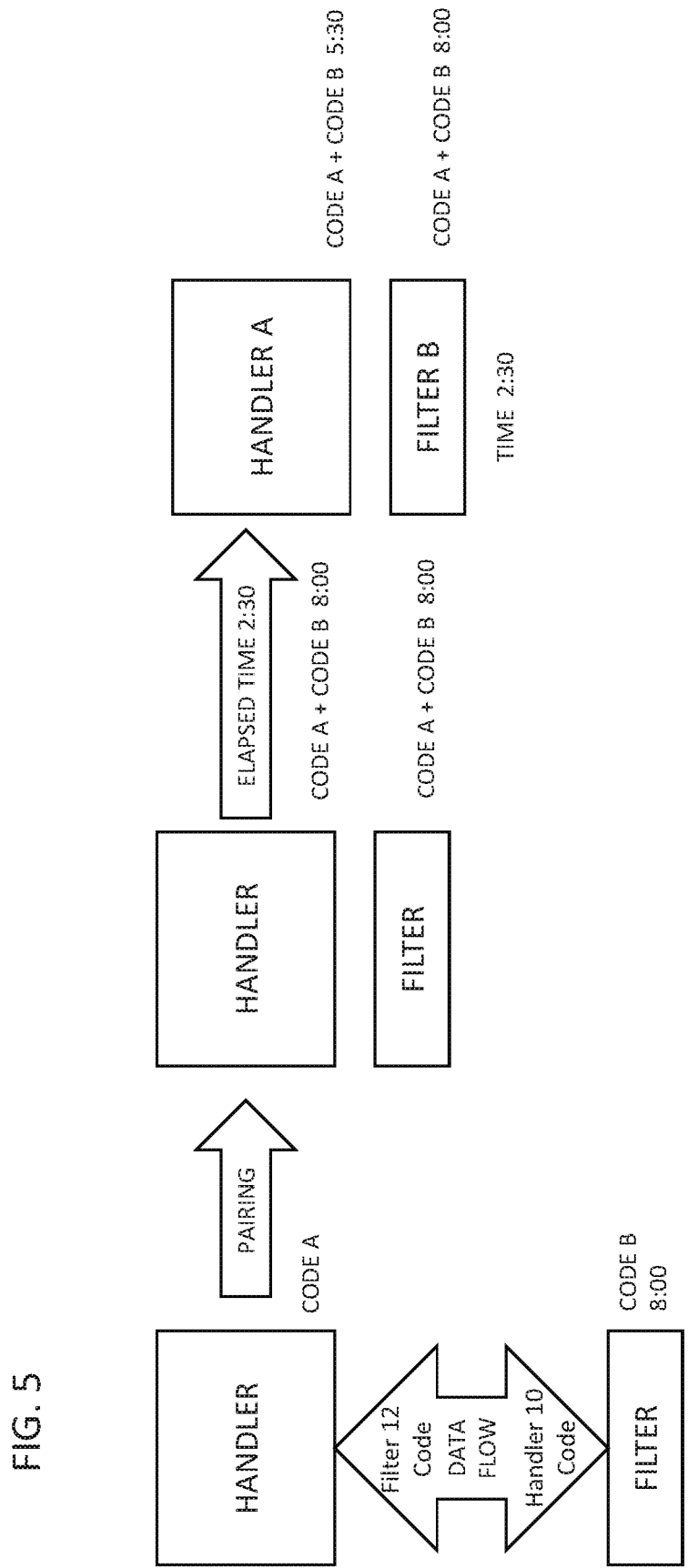
FIG. 5 is a schematic view of another embodiment illustrating the monitoring of the actual usage time for at least one filter and comparing it to its maximum predetermined filter usage time and the security system permitting the fluid handler (handler A in the illustration) to continue to operate as long as the at least one filter has useful life remaining.
Figure 6:
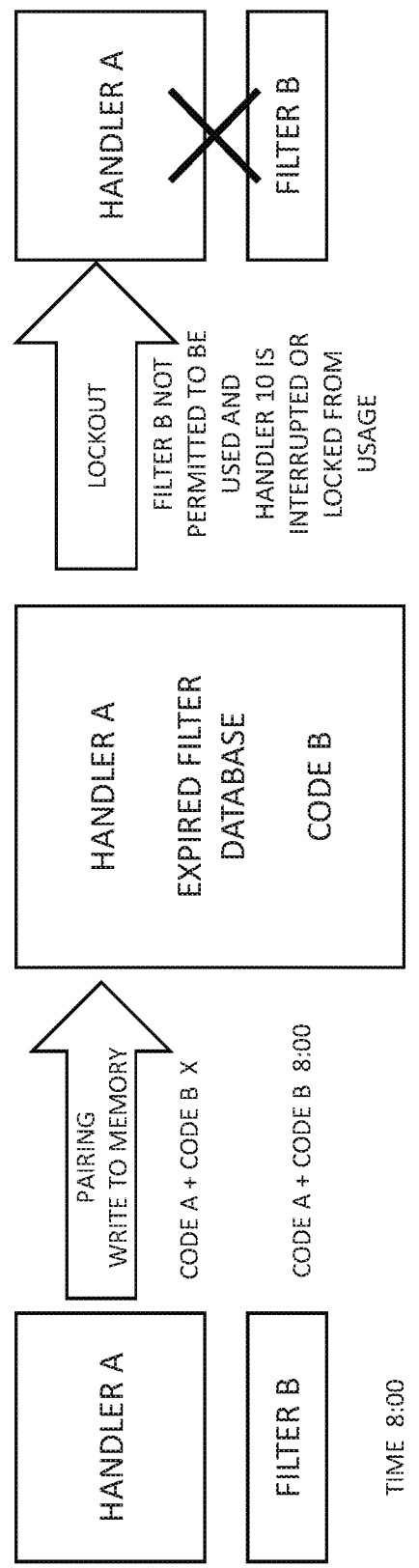
Figure 7:
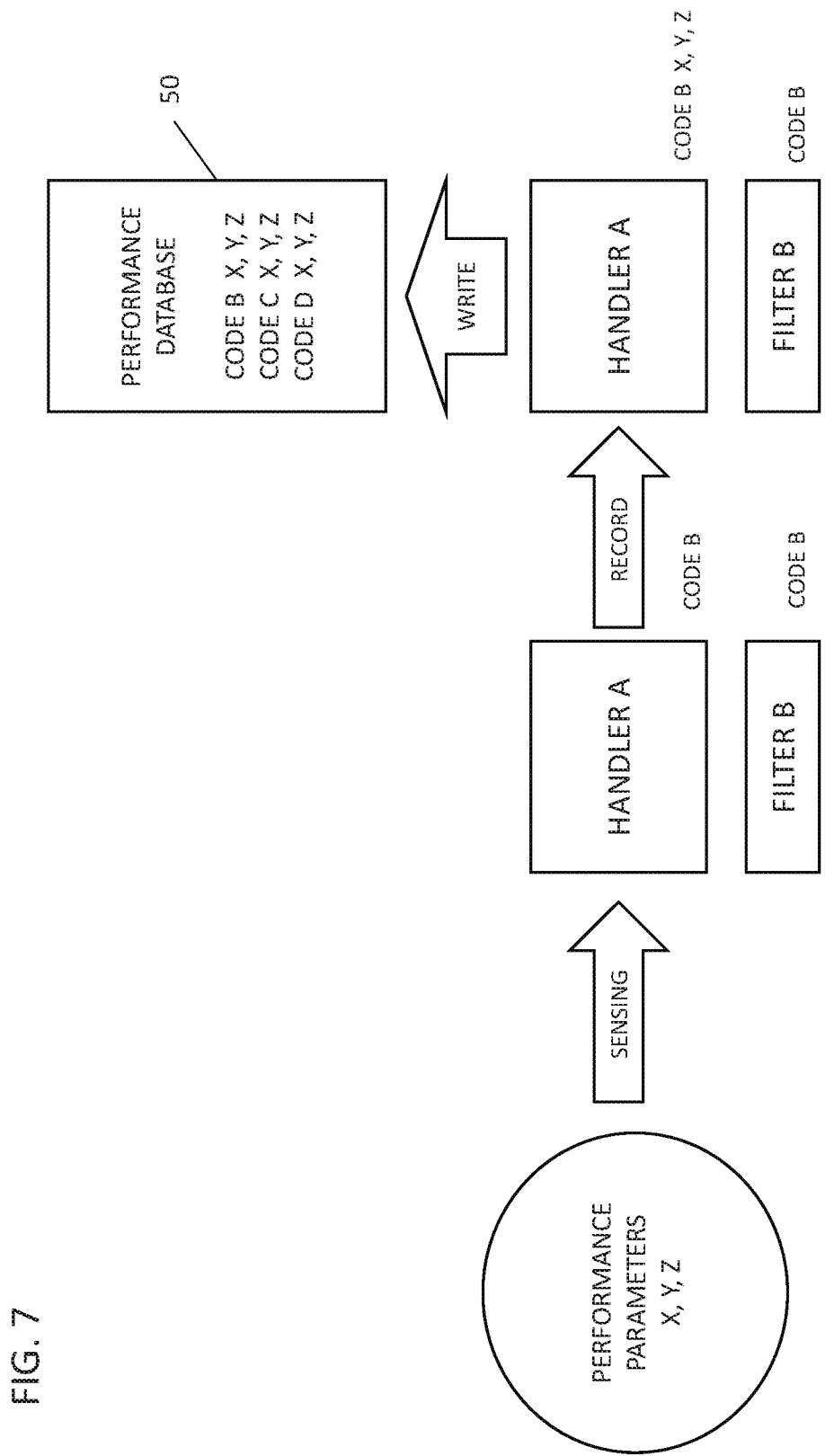

FIG. 6 is a view similar to FIG. 5 but instead showing the handler being interrupted and locked when the maximum predetermined filter usage time has been exceeded; and FIG. 7 is another schematic view illustrating the security system tracking of at least one or a plurality for performance parameters (identified X, Y and Z for ease of illustration) and subsequent writing of those parameters into a performance database for subsequent use by a user.

DETAILED DESCRIPTION OF THE PREFERRED EMBODIMENTS

Figure 1:
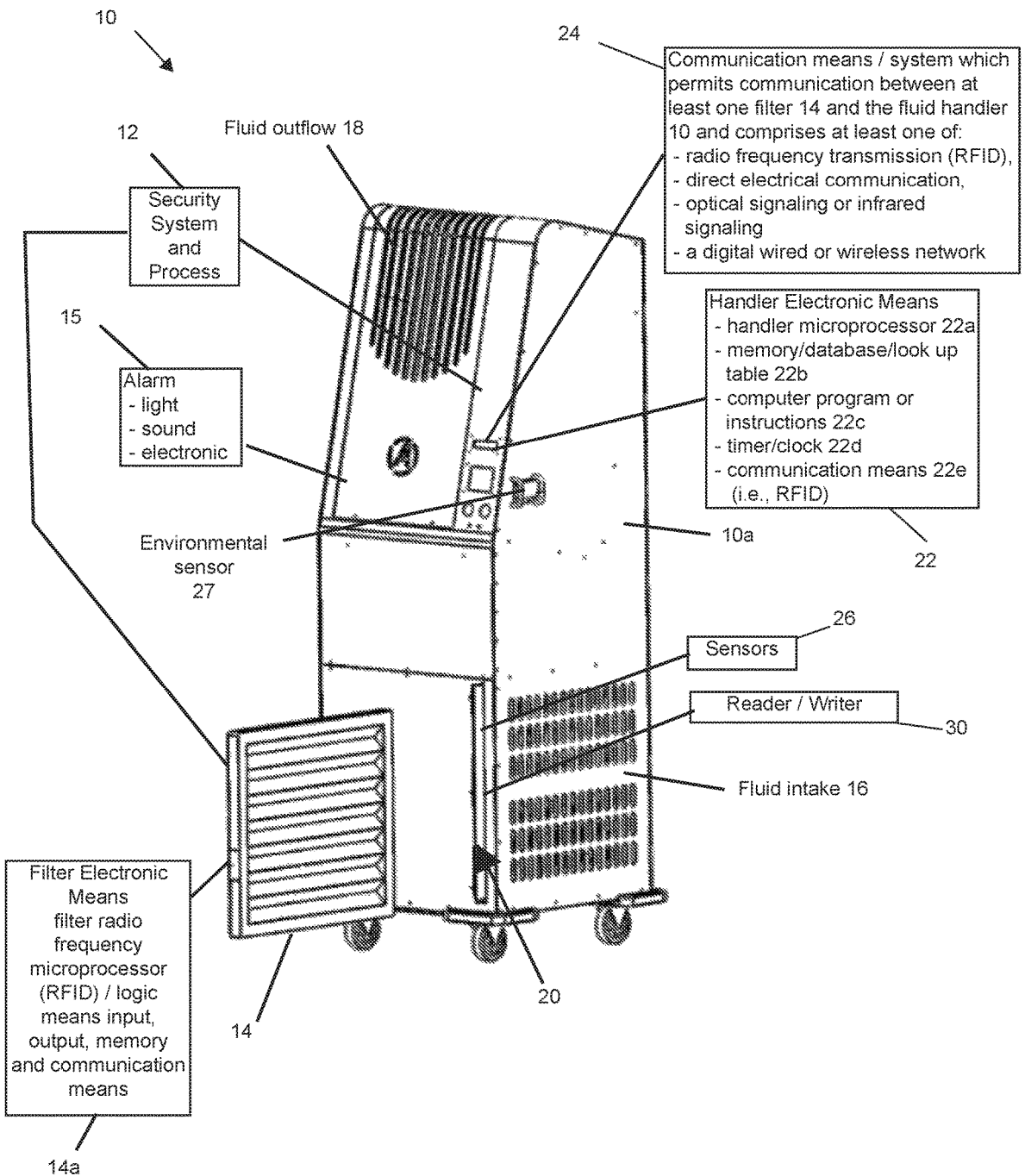
FIG. 1 is a perspective view of a fluid filtration device or handler having a security system and process in accordance with one embodiment of the invention.

Referring now to FIG. 1, a fluid filtration device or fluid handler 10 is shown in accordance with one embodiment of the invention. The fluid filtration device or fluid handler 10 is adapted to purify fluid from unwanted contaminants and comprises a housing 10a that houses various known components (e.g., a UV light source for irradiating fluid flow, such as airflow, a fan or blower control and the like) and a security system and process 12 which will be explained in more detail later herein. One exemplary fluid filtration device or fluid handler 10 is the fluid handler Model No. ILLUVIA® available from Aerobiotix, Inc., 444 Alexandersville Road, Miamisburg, Ohio 45342.

The security system and process 12 of the fluid filtration device or fluid handler 10 provides a digitally-based security system and process that facilitates ensuring proper filter usage and improving the overall fluid quality and treatment. The security system and process 12 comprises various hardware and software components located on both the at least one filter 14 and the fluid filtration device or fluid handler 10. In the embodiment being shown, the at least one filter 14 is a removable filter, such as a HEPA filter. The electronic means 14a resident on the at least one filter 14 and the fluid treatment processor 22a and the fluid filtration device or fluid handler 10 each comprise various digital and logic means having input, output and memory or memory means for storing information received from the fluid filtration device or fluid handler 10. The security system and process 12 also comprises computer programs or instructions 22c resident in a performance database or memory 22b on the fluid filtration device or fluid handler 10. Note that the electronic means 22 of the fluid filtration device or fluid handler 10 comprises a fluid treatment processor 22a, a conventional timer/clock 22d and memory 22b, which includes one or more databases or look-up tables and at least one or a plurality of databases or lookup tables resident in memory 22b and they will be described later herein.

The fluid filtration device or fluid handler 10 comprises a fluid outflow area or outlet 18 and a filter insertion slot 20 which is adapted and sized to receive the at least one filter 14. The fluid filtration device or fluid handler 10 and the at least one filter 14 each comprise electronic means 14a and 22e that permits bi-directional communication between the at least one filter 14 and the fluid filtration device or fluid handler 10. In one embodiment, the fluid filtration device or fluid handler 10 comprises a communication means or system 24 which has at least one of a radio frequency transmission means or device, such as an RFID device, a direct electrical communication, such as through a wired or wireless network, optical signaling or infrared signaling, or a digital wired or wireless network, all of which permit bi-directional communication between the at least one filter 14 and the fluid filtration device or fluid handler 10.

The fluid filtration device or fluid handler 10 further comprises at least one or a plurality of sensors 26, an environmental sensor 27 and at least one or a plurality of digital readers/writers 30 responsive to and under the control of the fluid treatment processor 22a, both of which are operatively related. Note that the at least one or a plurality of sensors 26 are associated with the filter insertion slot 20 as shown.

The communication means and system 22e of the fluid filtration device or fluid handler 10 communicates and cooperates with the electronic means 14a of the at least one filter 14 in order to bi-directionally transfer data between the at least one filter 14 and the fluid filtration device or fluid handler 10. Thus, the fluid filtration device or fluid handler 10 and the at least one filter 14 each comprise electronic and communication means and components to permit digital communication between the at least one filter 14 and the fluid filtration device or fluid handler 10. In this regard, each of the at least one filter 14 and the fluid filtration device or fluid handler 10 incorporate or have pre-programmed unique internal identification codes assigned thereto which will now be described.

In general, the fluid filtration device or fluid handler 10 comprises a unique fluid handler identification code and the at least one filter 14 comprises a unique filter identification code. When the at least one filter 14 is first inserted in the filter insertion slot 20, the fluid treatment processor 22a causes the fluid handler identification code to be written to the at least one filter 14 using the reader/writer 30 associated with the filter insertion slot 20. The fluid treatment processor 22a permanently records the fluid handler identification code into the memory of the at least one filter 14. Thus, the fluid filtration device or fluid handler 10 and the at least one filter 14 each have preprogrammed unique internal identification codes that are used to permanently pair the at least one filter 14 to the fluid filtration device or fluid handler 10. The electronic means 14a of the at least one filter 14 records the fluid handler 10 identification code in its memory. Note also that the reader/writer 30 of the fluid filtration device or fluid handler 10 also reads the unique filter identification code from the at least one filter 14 which is stored by the fluid treatment processor 22a in a performance database or memory 22b. It is important to note that during operation of the fluid filtration device or fluid handler 10 and as will be described later, the security system and process 12 utilizes the unique identification codes from the fluid filtration device or fluid handler 10 and the at least one filter 14 to, among other things, log the effectiveness of each of the individually serialized filters to determine if filter adulteration has taken place, preventing re-usage of the at least one filter 14 in more than one fluid filtration device or fluid handler 10 and preventing filter use for greater than its preprogrammed lifespan. In the illustration being described, the digitally-based data security system and process 12 utilizes the electronic means 14a and the electronic means 22 which are adapted to and capable of reading, writing and storage of data to achieve the security objectives, including, but not limited to, prevention of filter re-use, tampering or overuse. In the illustration being described, the security system and process 12 comprises one or more non-transient computer programs or instructions 22c resident in the performance database or memory 22b and utilize a processor algorithm or procedure resident in memory 22b which will now be described relative to FIG. 2. It should be understood that the references in FIG. 2 to other figures (e.g., FIG. 3, FIG. 4, etc.) further illustrate the operation being described therein.

In the illustration being described, the process begins at block 40 when a user inserts the at least one filter 14 into the fluid filtration device or fluid handler 10 and/or the fluid filtration device or fluid handler 10 is activated or turned on at block 42.

The procedure or routine proceeds to decision block 44 wherein the fluid filtration device or fluid handler 10 and the fluid treatment processor 22a determines whether or not the at least one filter 14 resident in the fluid filtration device or fluid handler 10 or that has been inserted into the fluid filtration device or fluid handler 10 comprises any fluid handler identification code. The fluid filtration device or fluid handler 10 and the fluid treatment processor 22a utilizes the reader/writer 30 to read the identification and pairing code information from the electronic means 14a resident on the at least one filter 14. In this regard, the at least one filter 14 and fluid filtration device or fluid handler 10 may comprise the radio frequency identification device (RFID) of the communication means or system 24 mentioned earlier that facilitates bi-directional communication, identification and pairing of the at least one filter 14 to the fluid filtration device or fluid handler 10 in a manner that is conventionally known.

If the fluid treatment processor 22a determines that a fluid handler identification code for the fluid filtration device or fluid handler 10 is not permanently written to the at least one filter 14, then the fluid treatment processor 22a causes the reader/writer 30 to permanently write the unique fluid handler identification code from the fluid filtration device or fluid handler 10 to be permanently written to the at least one filter 14 (block 46). Thereafter, the routine proceeds to block 48 wherein the fluid treatment processor 22a reads the filter identification code and a maximum filter usage time or preprogrammed lifespan or maximum filter usage code using the reader/writer 30 and causes them to be stored in the performance database or memory 22b of the fluid filtration device or fluid handler 10.

If it is determined at decision block 44 that the at least one filter 14 has a fluid identification code stored in the electronic means 14a of the at least one filter 14, then the routine proceeds to block 62 wherein the fluid treatment processor 22a verifies that the fluid handler identification code, as read from the at least one filter 14 using the reader/writer 30, matches the unique fluid handler identification code for the fluid handler 10 in which the at least one filter 14 is located. The fluid treatment processor 22a also causes the reader/writer 30 to read the filter identification code and compares it against a filter identification code database.

At decision block 64, it is determined whether the fluid handler identification code read from the at least one filter 14 is verified against the database (i.e., is already resident or matches the code stored in the database). In this regard, the fluid treatment processor 22a determines whether the fluid handler identification code associated and stored on the at least one filter 14 is the correct fluid handler identification code, meaning that it is the same fluid handler identification code for the fluid filtration device or fluid handler 10 into which the at least one filter 14 is inserted. If the fluid handler identification code read from the at least one filter 14 is not verified against the database resident on the fluid filtration device or fluid handler 10, then the fluid treatment processor 22a causes the fluid handler operation to be interrupted and/or prevents the fluid filtration device or fluid handler 10 from operating as shown in block 66. In other words, the fluid treatment processor 22a causes the at least one filter 14 to be rejected, thereby preventing the at least one filter 14 from being used not only in the fluid filtration device or fluid handler 10, but also in subsequent fluid filtration devices or fluid handlers 10. In this regard, the fluid treatment processor 22a of the fluid filtration device or fluid handler 10 may cause a permanent "do not use" message or other notice to be permanently written to the at least one filter 14 so that it cannot be used again, for example, in another fluid filtration device or fluid handler having the features of the fluid filtration device or fluid handler 10.

At block 68, an alarm 15 (FIG. 1) or notification is activated to notify the user that the at least one filter 14 cannot be used. In this regard, the alarm 15 or notification may comprise a light, sound, electronic notice, email or other communication to the user. Returning to FIG. 2, after block 68, the alarm 15 or notification notifies the user and the user may take action, such as replacing the at least one filter 14. The routine then loops back to block 42 as shown.

If the decision at decision block 64 is affirmative, then the fluid filtration device or fluid handler 10 operates normally at block 50. During operation, however, the fluid treatment processor 22a and the security system and process 12 continually monitor the operation of the fluid filtration device or fluid handler 10 and the at least one filter 14. At block 52, the fluid filtration device or fluid handler 10 senses and stores or collects filter-specific performance data and records that performance data into the performance database or memory 22b. The parameters X, Y and Z monitored and saved in the illustration being described include fluid quality, as sensed by the sensors 26, fluid flow through the at least one filter 14, power draw on the fluid filtration device or fluid handler 10, all of which assist in identifying the effectiveness of the at least one filter 14. The sensors 26 and 27 may comprise a particle sensor, a carbon dioxide ($CO_2$) sensor, a barometric sensor or the like. It should be understood that timing or other parameters may be used to determine the system security, integrity and effectiveness of the at least one filter 14 resident on the fluid filtration device or fluid handler 10. In the illustration, the sensors 26 and 27 may provide sensed readings of pressure across the at least one filter 14, with a large pressure drop generally corresponding to a clogged or contaminated filter, and a low pressure drop generally correlating to the at least one filter 14 being unclogged. Likewise, airflow readings across the at least one filter 14 may also indicate a clogged filter if the airflow through the at least one filter 14 is reduced to below a predetermined flow rate which provides an indication of a clogged filter.

At block 54, the fluid treatment processor 22a and/or a user evaluates and uses the performance database or memory 22b to determine the performance and/or the integrity of the current at least one filter 14 or of any previously paired at least one filter 14 that is inserted into the fluid filtration device or fluid handler 10. Thereafter, it is determined at decision block 56 whether an actual usage time for the at least one filter 14 is greater than a predetermined maximum usage time for the at least one filter 14. If the predetermined maximum usage time is exceeded, then the fluid treatment processor 22a interrupts or prevents (block 70) the fluid filtration device or fluid handler 10 from operating and causes an expiration notice or code to be permanently written to the at least one filter 14. At block 72, the routine continues to provide an alarm or notification to the user as mentioned earlier herein relative to block 68, and the user may take action, such as replacing the at least one filter 14. Thereafter, the routine loops back to block 42 as shown.

If the decision at decision block 56 is negative, then it is determined at decision block 58 whether or not it is desired to continue fluid handler operation in view of the fact that the filter actual usage time is not greater than the maximum filter usage time for the at least one filter 14. If it is desired to continue fluid handler operation, then the routine loops back to block 50 as shown. If it is not desired to continue fluid handler operation, then the fluid filtration device or fluid handler 10 may be deactivated or turned off automatically or by a user or the fluid handler operation is terminated or interrupted as shown at block 60. After block 60, the routine loops back to block 42 as shown.

Referring now to FIGS. 3-7, various illustrative examples of the operation of the security system and process 12, the fluid filtration device or fluid handler 10 and the at least one filter 14 will now be described. For ease of illustration, the at least one filter 14 is identified in FIGS. 3-7 as filter or filter B and the fluid filtration device or fluid handler 10 is identified as handler or handler A. In the illustration being described, the fluid handler identification code and the filter identification code can be alphabetic, alphanumeric, digital (such as binary or hexadecimal) or the like.

Figure 3:
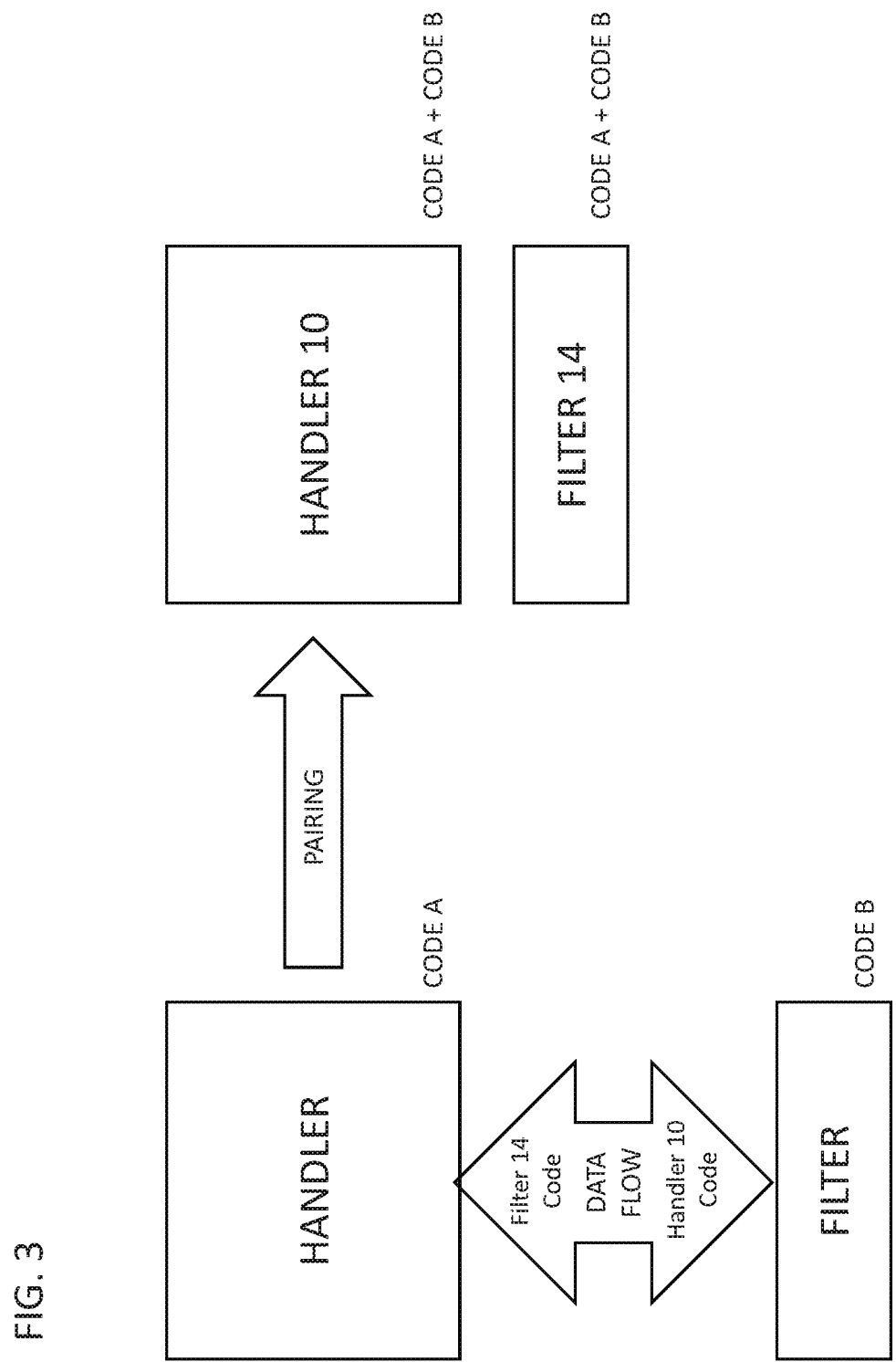
FIG. 3 is a schematic diagram showing a basic pairing of a filter having a filter identification code with a fluid handler identification code for a fluid handler.

As illustrated in FIG. 3, note that the fluid filtration device or fluid handler 10 and fluid treatment processor 22a generates a pairing code comprising the combination or summation of codes A and B stored in the performance database or memory 22b of the fluid filtration device or fluid handler 10. Likewise, the at least one filter 14 has the pairing code, which is the combination of code A and code B, permanently stored thereon. As mentioned earlier, code A and code B can be simply combined, summed or otherwise processed to provide a unique pairing code for the fluid filtration device or fluid handler 10 and the at least one filter 14. It should also be understood that the identification codes and the pairing code may be encrypted if desired by suitable encryption algorithms (not shown) stored in the performance database or memory 22b on the fluid filtration device or fluid handler 10.

As mentioned relative to block 62 and decision block 64 (FIG. 2), when the at least one filter B (FIG. 4) is inserted into a second different fluid filtration device or fluid handler C (i.e., other than fluid filtration device or fluid handler A), the second fluid filtration device or fluid handler C does not permit operation because the at least one filter B was previously paired with the fluid filtration device or fluid handler A, assuming in the illustration that the second fluid filtration device or fluid handler C comprises the same features and components of the fluid filtration device or fluid handler A. Note at the left-hand side of FIG. 4, the at least one filter B is inserted into the fluid filtration device or fluid handler A and the pairing occurs. If a user now inserts the at least one filter B into a different fluid filtration device or fluid handler (labeled handler C in the illustration), the handler C interrupts or prevents the fluid handler C from operating because it will reject the filter B as not being previously paired with the handler C. In this regard, recall that the fluid filtration device or fluid handler 10 and each handler that receives the at least one filter 14 reads the pairing code from the at least one filter 14 and compares the handler portion of the code (i.e., code A in the illustration) against the codes in the performance database or memory 22b that has the pairing code of handler identification code A and the at least one filter identification code B stored therein. When the fluid treatment processor 22a receives the pairing code from the filter B it immediately identifies that the code A, associated with the handler A, is not the correct code because the filter B was inserted into a different handler (i.e., handler C in the example), which means that the at least one filter 14 was not previously or originally paired with the handler C. In response, the fluid treatment processor 22a of handler C interrupts or does not permit the handler C to operate.

It should be understood, that the fluid treatment processor 22a of the handler C also compares the at least one filter identification code (code B in the illustration) against a filter database and if it determines that the filter identification code is not stored in the database, then the fluid treatment processor 22a of handler C will not permit the handler C to operate or if it is operating then to interrupt that operation. As mentioned earlier relative to block 68 in FIG. 2, the security system and process 12 may issue an alarm or notice to the user so that the user can take appropriate action, such as replacing the at least one filter 14 with either a filter that has been paired with handler C and that has useful life remaining or with a new filter that can then be paired with handler C as explained at blocks 46 and 48 in FIG. 2.

Referring now to FIG. 5 and as mentioned earlier herein, the fluid treatment processor 22a of the fluid filtration device or fluid handler 10 causes the filter identification code for the at least one filter 14 to be stored in the performance database or memory 22b as well as a maximum filter usage time code associated with the maximum filter usage time to be read and stored in the performance database or memory 22b. The security system and process 12 utilizes usage time to interrupt the fluid filtration device or fluid handler 10 from operating or to terminate the operation of the fluid filtration device or fluid handler 10 in the event the maximum filter usage time has been exceeded. These features are described earlier herein relative to blocks 48, 56, 70 and 72.

As with the embodiment in FIG. 3, note that the typical pairing occurs (FIG. 5) between the at least one filter 14 and the fluid filtration device or fluid handler 10. Note that the pairing is the same except that in the illustration in FIG. 5, a maximum filter usage time is also permanently stored on the at least one filter 14 and read by the reader/writer 30, and the fluid treatment processor 22a stores the predetermined maximum filter usage time (8 hours in the illustration being described) into the performance database or memory 22b. In this regard, note that the performance database or memory 22b on the fluid filtration device or fluid handler 10 comprises the handler identification code, the combined pairing code which includes the handler identification code and the filter identification code or some variation or derivative thereof so that the at least one filter 14 is paired with the fluid filtration device or fluid handler 10.

As shown in FIG. 5, note that the 8 hour maximum filter usage time is also stored in the performance database or memory 22b and associated with the unique filter identification code for the at least one filter 14. It should be noted that the performance database or memory 22b may comprise a look-up table to enable the fluid treatment processor 22a to easily look up parameter data, such as the cumulative actual usage time and maximum filter usage time for a particular filter. In the illustration being described, the fluid treatment processor 22a and fluid filtration device or fluid handler 10 monitors the hourly usage of the at least one filter 14 and updates the performance database or memory 22b for a cumulative elapsed usage time, which is 2½ hours in the illustration being described. FIG. 5 shows an illustration where the actual usage elapsed time for the at least one filter 14 has not exceeded its predetermined maximum usage time, which time has not elapsed or expired. The fluid treatment processor 22a of the fluid filtration device or fluid handler 10 updates the performance database or memory 22b with the remaining usage time. Thus, note in the right hand side of FIG. 5 that the remaining time (5½ hours in the illustration) is associated with the pairing code (code A+code B) and stored in the lookup table or database. Note that the filter B still has the permanently associated 8 hour maximum predetermined usage time stored in memory on the at least one filter 14 and this association is permanent on the at least one filter 14.

Figure 4:
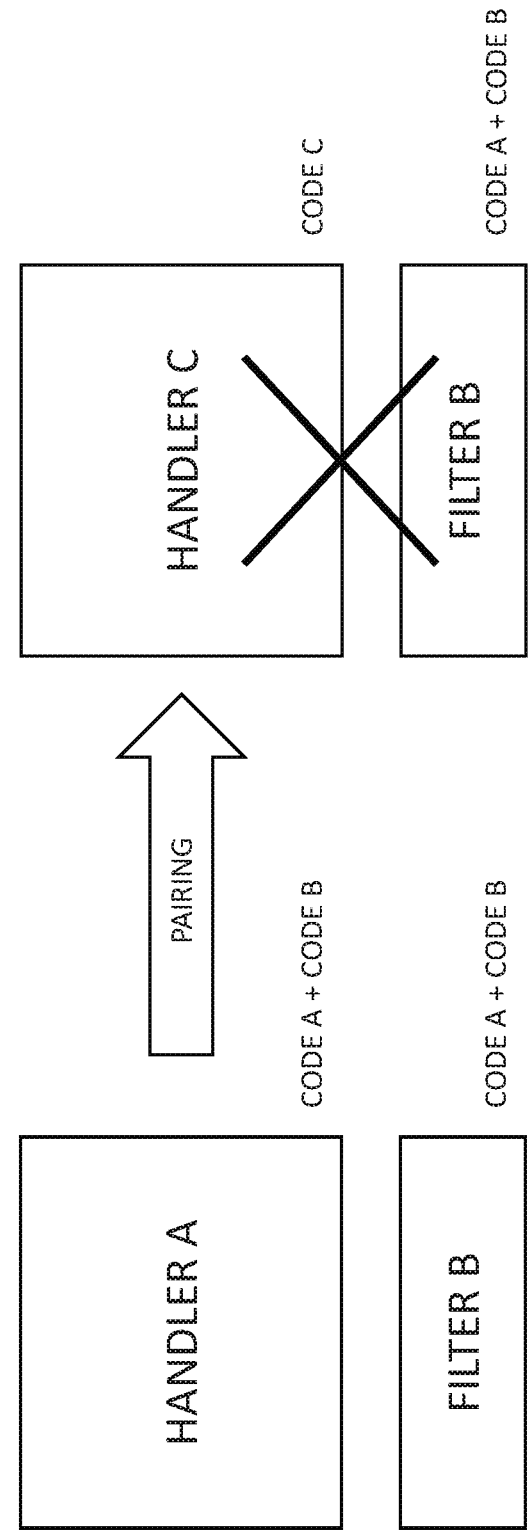
FIG. 4 is a schematic diagram illustrating a filter having been paired with a first handler (handler A) being inserted or attempted to be paired with a second handler (handler C) and illustrating that the pairing with handler C does not occur.

In contrast, FIG. 6 shows an illustration similar to FIG. 4, except that the maximum predetermined filter usage time has been exceeded. Note in the left-hand side of FIG. 6, the pairing occurs as described earlier herein and the maximum filter usage time (8 hours in the illustration) is written to memory or database as described and stored in the memory of the fluid filtration device or fluid handler 10 along with the unique pairing code. The fluid filtration device or fluid handler 10 stores the filter identification code in an expired filter database which is stored in the performance database or memory 22b of the fluid filtration device or fluid handler 10. Thereafter, when the at least one filter 14 is inserted into the filter insertion slot 20 and the reader/writer 30 reads the filter identification code (code B in the illustration being described), the fluid treatment processor 22a peruses the expired filter database or lookup table for the filter identification code. If it finds that same code in the expired filter database, it locks out the fluid filtration device or fluid handler 10 or interrupts or prevents the fluid filtration device or fluid handler 10 from operating. In this case, it rejected the at least one filter 14 because actual usage time exceeded the predetermined maximum usage time, thereby preventing the at least one filter 14 from being used once it has exceeded its maximum filter usage time, as previously explained and described relative to blocks 56 and 70 in FIG. 2.

Thereafter, an alarm or notification is provided to the user so that the user can take appropriate action, such as replace the at least one filter 14 with another filter that either has been paired with the fluid filtration device or fluid handler 10 or that can be paired with the fluid filtration device or fluid handler 10 and that has useful time left for its maximum filter usage time.

Referring now to FIG. 7 and as mentioned earlier herein relative to blocks 52 and 54 in FIG. 2, various performance data and characteristics are sensed, monitored, collected and stored by the fluid filtration device or fluid handler 10 in the performance database or memory 22b. In this regard, the system monitors various performance parameters, which in the example are represented by letters X, Y and Z, associated with the fluid filtration device or fluid handler 10 and the at least one filter 14. These parameters X, Y and Z may include, but are not limited to, fluid quality (i.e., air quality both at the fluid intake 16 and the fluid outflow area or outlet 18) as sensed by at least one or a plurality of sensors, such as the environmental sensor 27 or the other sensors 26 associated with the fluid filtration device or fluid handler 10. The parameters X, Y and Z may also include fluid flow through the filter, with the general understanding that as the filter is used, the fluid flow through the filter becomes less. Another parameter may be a power draw on the fluid filtration device or fluid handler 10 with the understanding that as the at least one filter 14 becomes used or dirty, the power draw or consumption by the blower is increased which provides an indication that the at least one filter 14 is dirty or clogged. Still another parameter is the timing or other parameters determining system integrity, such as pressure drop or airflow drop across the at least one filter 14, as mentioned earlier herein, as measured by the sensors 26 and 27.

Figure 2:
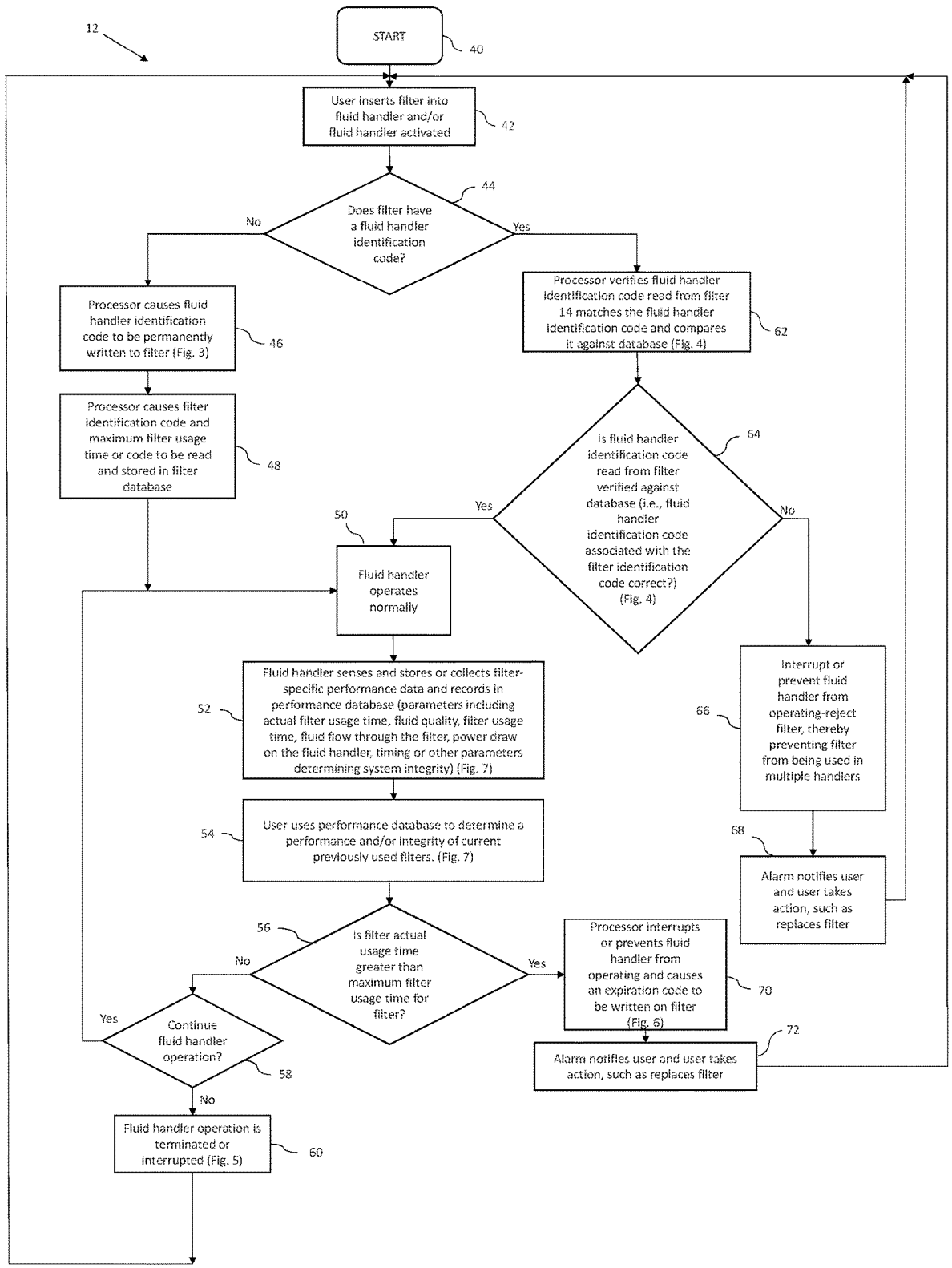
FIG. 2 is a schematic diagram of the processor procedure to facilitate providing the security system and process to at least one filter.

As mentioned relative to block 54 in FIG. 2, the user uses the performance data in the performance database of the fluid treatment processor 22a to determine a performance and/or integrity of current or previously used filters. The fluid filtration device or fluid handler 10 senses the various performance parameters X, Y and Z using at least one or a plurality of sensors, such as sensors 25 and 26, and after a filter, such as the at least one filter 14, is received in the filter insertion slot 20 of the fluid filtration device or fluid handler 10 and paired as described earlier herein relative to FIG. 3, the fluid treatment processor 22a of fluid filtration device or fluid handler 10 records the various parameter information in the performance database or memory 22b. It should be understood that the fluid filtration device or fluid handler 10 may have a single database or memory 22b that stores all the information mentioned herein or it may have a plurality of databases or lookup tables that can be accessed and used by the fluid treatment processor 22a.

As illustrated in FIG. 7, after the pairing of the at least one filter 14 to handle A, the fluid filtration device or fluid handler 10 associates the performance parameters X, Y and Z and associates the parameters X, Y and Z with that particular filter (i.e., the at least one filter 14). Once the performance parameters X, Y and Z are monitored and stored or written to the performance database or memory 22b, the user can use the at least one or a plurality of parameters X, Y and Z to control an operation of the fluid filtration device or fluid handler 10 to monitor the performance of the at least one filter 14. For example, if the fluid filtration device or fluid handler 10 senses a significant power draw after only a few hours of operation or use of the at least one filter 14 in the fluid filtration device or fluid handler 10, such performance characteristic can be associated with that filter so that the user can make informed performance, usage and control decisions. For example, if a user utilizes a particular brand of filter, but finds that compared to another brand of filter of equal value, the first filter is less desirable because the fluid quality and contamination of fluid flowing the filter is higher than the fluid quality of air passing through the second filter, then the user can discard the first filter in favor of the more effective quality filter.

Monitoring the various parameters is important and provides means and procedure for improving the decontamination or treatment of air flowing out of the fluid filtration device or fluid handler 10, which improves the overall performance of the fluid filtration device or fluid handler 10 and generally improves the ability of the fluid filtration device or fluid handler 10 to decontaminate and treat the fluid passing through the fluid filtration device or fluid handler 10.

Perhaps, even more importantly is the improved safety and operation of the fluid filtration device or fluid handler 10. Using the effectiveness of the security system and process 12 described herein facilitates ensuring that the effectiveness, adulteration or overuse of the at least one filter 14 will not occur.

In the illustration being described, the fluid filtration device or fluid handler 10 is placed in a room, such as a hospital room, surgery center, surgery room, building or other room in which the fluid filtration device or fluid handler 10 can operate. Once situated or located in the desired location, the fluid filtration device or fluid handler 10 can operate as described herein to effectively reduce contaminants, airborne bacteria and other pathogens. The security system and process 12 described herein facilitates reducing or eliminating altogether usage of a filter that is contaminated to an undesired level, that has exceeded its predetermined maximum usage time, or that due to one or more other parameters X, Y and Z, is desired not to be used.

Additional Considerations and Summary of Important Features and Results

1. The security system and process 12 for the fluid filtration device or fluid handler 10 may comprise the electronic means 14a and 22 for transferring data bidirectionally between a changeable filter, such as the at least one filter 14 and the fluid filtration device or fluid handler 10. The at least one filter 14 and the fluid filtration device or fluid handler 10 also incorporate the preprogrammed unique internal identification codes.

2. As explained, upon initial installation of at least one filter 14 to the fluid filtration device or fluid handler 10, the fluid filtration device or fluid handler 10 transfers and records the unique handler identification code to the at least one filter 14. The least one filter 14 then receives and records the unique handler identification code. The fluid filtration device or fluid handler 10 further comprises receiving means to receive the unique filter identification code from the at least one filter 14 and then compares the unique handler identification code which originated in or is received by the at least one filter 14 to a filter handler identification code.

The security system and process 12 provides the lockout means to prevent the fluid filtration device or fluid handler 10 from functioning if the handler identification code received from the at least one filter 14 does not match its internal handler identification code, thereby preventing the use of an individual filter, such as the at least one filter 14, in more than one fluid filtration device or fluid handler 10.

3. The security system and process 12 initiates timing codes clocking the filter usage time and pairs or associates it with the filter identification code. The security system and process 12 provides limit means or a lock out that prevents the fluid filtration device or fluid handler 10 from functioning if a predetermined filter running time has elapsed. The security system and process 12 further allows for individual filter removal and re-installation, without loss of timing data.

4. The security system and process 12 provides limit means to prevent the fluid filtration device or fluid handler 10 from functioning if a filter usage time has expired and further encodes and retains a database of expired filter identification codes, thus preventing the re-use of an expired filter, such as the at least one filter 14.

5. The security system and process 12 where all new filters, such as the at least one filter 14, when installed in the fluid filtration device or fluid handler 10 communicates a unique filter identification code to the fluid filtration device or fluid handler 10, the fluid filtration device or fluid handler 10 checks the unique filter identification code against a database of expired codes and prevents operation if a new filter identification code for a new filter is present in the database.

6. The security system and process 12 wherein the fluid filtration device or fluid handler 10 transmits an expiration code upon expiration of the filter. This expiration code is received by the at least one filter and is used to prevent the at least one filter 14 from being used in response to the expiration code.

7. The security system and process 12 wherein a predetermined filter running time is encoded in the at least one filter 14. The security system and process 12 allows for different filter types with varying predetermined filter running times to be received by the fluid filtration device or fluid handler 10 and the fluid filtration device or fluid handler 10 enacts expiration timing specific for the filter type.

8. The security system and process 12 for the fluid filtration device or fluid handler 10 comprises a database which receives and encodes a unique identification code originating in an individual filter, such as the at least one filter 14, and pairs the unique identification code with system performance data. The unique identification code and the performance data allow a user to evaluate the performance of the at least one filter 14. The performance data may consist of fluid quality, fluid flow, power draw, timing, or other parameters determining system integrity.

9. The communication means of the electronic means 14a and 22 between the at least one filter 14 and the fluid filtration device or fluid handler 10 may be via radiofrequency transmission, direct electrical contact, optical signaling, infrared signal, or via a wired or wireless digital network.

10. The security system and process 12 where the at least one filter 14 and the fluid filtration device or fluid handler 10 comprise logic means which may consist of input, output, and memory means.

11. The encoding and/or transmission of handler and/or filter data may be encrypted if desired.

12. The embodiment described provides an effective method for programming a security system and process 12 for a fluid filtration device or fluid handler 10 and comprising the steps of:
   programming the fluid filtration device or fluid handler 10 with an identification code unique to the fluid filtration device or fluid handler 10;
   installing the at least one filter 14 in the fluid filtration device or fluid handler 10;
   initiating transference of the identification code to the at least one filter 14; and
   exclusively pairing the at least one filter 14 to the fluid filtration device or fluid handler 10 such that the at least one filter 14 cannot be used in any other fluid handler, such as the fluid filtration device or fluid handler 10, other than the one to which it was paired.

13. The embodiment described provides an effective method for programming a security system and process 12 for the fluid filtration device or fluid handler 10 comprising the steps of
   installing a fluid filter in the fluid filtration device or fluid handler 10;
   bidirectionally transferring unique identification codes between the fluid filtration device or fluid handler 10 and the at least one filter 14 resulting in an exclusive pairing of the at least one filter 14 to the fluid filtration device or fluid handler 10; and
   initiating a timing means to clock the usage time of the at least one filter 14 in the fluid filtration device or fluid handler 10.

Advantageously, the embodiments shown and described herein could be used alone or together and/or in combination with one or more of the features covered by one or more of the claims set forth herein, including but not limited to one or more of the features or steps mentioned in the Summary of the Invention and the claims.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. A fluid filtration security system for decontaminating or treating air in an environment, comprising:
- a fluid handler having a housing having at least one filter receiving area for receiving at least one filter with said at least one filter having a filter memory, said fluid handler having a fluid handler identification code associated therewith that is unique to said fluid handler, said fluid handler comprising a reader/writer for reading and writing information on said at least one filter and said at least one filter having at least one filter identification code associated therewith, said fluid handler having a blower that causes air flow in said fluid handler in order to treat the air to facilitate reducing or eliminating airborne contaminants, bacteria or pathogens in the air as it passes through said fluid handler; and
- a fluid treatment processor for generating at least one pairing identification code in response to said fluid handler identification code and said at least one filter identification code;
- wherein said fluid treatment processor controls an operation of said fluid handler and at least one of logs a filter effectiveness associated with said at least one filter, prevents a re-usage of said at least one filter if said at least one filter fails at least one predetermined filter usage criteria, or prevents use of said at least one filter if a usage time of said at least one filter exceeds a predetermined usage time or if said fluid handler identification code of said at least one pairing identification code does not match said fluid handler identification code for said fluid handler;
- wherein said fluid handler maintains a database or lookup table of said at least one pairing identification code and said at least one filter identification code;
- wherein said fluid treatment processor causes said fluid handler identification code that is unique to said fluid handler to be written to said at least one filter using said reader/writer and said fluid treatment processor permanently records said fluid handler identification code into said filter memory of said at least one filter and generates said at least one pairing identification code in response thereto in order to permanently pair said at least one filter to said fluid handler, said reader/writer of said fluid handler being adapted to read said at least one filter identification code that is unique to said at least one filter and said fluid treatment processor stores said at least one filter identification code that is unique to said at least one filter and said at least one pairing code into said database in a fluid handler memory associated with said fluid handler;
- wherein if said fluid treatment processor determines that said fluid handler identification code for said fluid handler is neither part of said at least one pairing identification code nor permanently written to said filter memory of said at least one filter when said at least one filter is situated in said at least one filter receiving area, then said fluid treatment processor causes said reader/writer to permanently write said fluid handler identification code associated with said fluid handler to said filter memory of said at least one filter and reads said at least one filter identification code and performance data comprising at least one of a maximum filter usage time, preprogrammed lifespan or maximum filter usage code using said reader/writer and causes them to be stored in said database into said fluid handler;
- wherein said fluid treatment processor reads said fluid handler identification code from said at least one filter when said at least one filter is received in said at least one filter receiving area and verifies that said fluid handler identification code is already resident in said filter memory of said at least one filter or matches said fluid handler identification code stored for that particular said at least one filter in said database and determines whether said fluid handler identification code associated and stored on said at least one filter is the same fluid handler identification code for said fluid handler as originally written to said filter memory when it was inserted into said fluid handler;
- wherein if said fluid handler identification code read from said at least one filter is not verified against said database, then said fluid treatment processor causes the fluid handler operation to be interrupted and/or prevents said fluid handler from operating, thereby preventing said at least one filter from being used in either said fluid handler or any subsequent fluid handler;
- wherein said environment comprises at least one indoor room, said blower in said fluid handler causing at least some contaminated air in said environment to enter into said fluid handler in order to treat said contaminated air;
- wherein at least a portion of said contaminated air passes through said at least one filter so that said at least one filter may collect at least some of said contaminated when said fluid handler is active and so that said fluid handler may deliver decontaminated or treated air into said environment.

2. The fluid filtration security system as recited in claim 1 wherein said fluid treatment processor programs said at least one filter with said fluid handler identification code when said at least one filter is received in said at least one filter receiving area and generates said at least one pairing identification code in response thereto;
- said fluid treatment processor subsequently preventing or locking out said fluid handler from operating if said at least one filter identification code of said at least one filter that is received in said at least one filter receiving area of said fluid handler does not match said fluid handler identification code for said fluid handler.

3. The fluid filtration security system as recited in claim 1 wherein said fluid handler comprises said reader/writer associated with said at least one filter receiving area and said at least one filter comprises at least one of a filter processor or said filter memory on said at least one filter, said fluid treatment processor communicating said fluid handler identification code to said at least one of said filter processor or said filter memory when said at least one filter is received in said at least one filter receiving area;
- said reader/writer also being adapted to read said at least one of said filter identification code, said fluid handler identification code or said at least one pairing identification code to permit said fluid treatment processor to control said fluid handler in response thereto.

4. The fluid filtration security system as recited in claim 3 wherein said at least one filter has an associated predetermined useful life, said fluid treatment processor preventing or interrupting said fluid handler if an actual use life of said at least one filter exceeds said predetermined usage time.

5. The fluid filtration security system as recited in claim 4 wherein said fluid treatment processor stores said predetermined usage time into said database when said at least one filter is inserted in said at least one filter receiving area.

6. The fluid filtration security system as recited in claim 3 wherein said reader/writer reads said at least one filter identification code and said fluid treatment processor receives said at least one filter identification code and combines it with said fluid handler identification code and creates said at least one pairing identification code in response thereto, said fluid treatment processor preventing said fluid handler from operation if at least one of the following conditions occurs:
   said fluid handler identification code of said at least one pairing identification code does not match said fluid handler identification code for said fluid handler in which said at least one filter is received; or
   a predetermined usage for said at least one filter exceeds said predetermined usage time.

7. The fluid filtration security system as recited in claim 3 wherein said fluid filtration security system comprises verification means for preventing said at least one filter from being used in different fluid handlers.

8. The fluid filtration security system as recited in claim 7 wherein said verification means comprises said fluid treatment processor that causes said reader/writer to write or store said fluid handler identification code onto a data receiver located on said at least one filter, said fluid handler also creating said at least one pairing identification code by combining or processing said fluid handler identification code with said at least one filter identification code which said fluid handler stores in memory;
   said fluid treatment processor comparing the fluid handler identification code stored on each of said at least one filter that is received in said at least one filter receiving area with said fluid handler's identification code and interrupting or locking said fluid handler from operation if they are different.

9. The fluid filtration security system as recited in claim 8 wherein said fluid treatment processor permanently causes said fluid handler identification code to be stored or written to said data receiver of said at least one filter.

10. The fluid filtration security system as recited in claim 1 wherein upon installation of said at least one filter into said at least one filter receiving area, said fluid treatment processor initiates a timer or clock that clocks a usage time for said at least one filter, said fluid treatment processor interrupting or preventing said fluid handler from running if said usage time exceeds a predetermined usage time for said at least one filter.

11. The fluid filtration security system as recited in claim 10 wherein said fluid treatment processor causes said usage time to be stored in said filter memory and associated with said at least one pairing identification code so that said at least one filter can be removed or re-installed without loss of any remaining said usage time.

12. The fluid filtration security system as recited in claim 1 wherein said fluid handler comprises said database or lookup table for storing expiration data by said at least one filter identification code for any said at least one filter having said usage time that exceeds said predetermined usage time of said at least one filter, said fluid treatment processor recording an expired filter indicator in said database or lookup table and interrupting or preventing said fluid handler from operating if said fluid treatment processor determines that said at least one filter that is received in said at least one filter receiving area has expired.

13. The fluid filtration security system as recited in claim 1 wherein said fluid treatment processor tracks an actual usage time for said at least one filter, and associates said actual usage time with said at least one pairing identification code;
   said fluid treatment processor preventing or terminating operation of said fluid handler if said actual usage time exceeds said predetermined usage time.

14. The fluid filtration security system as recited in claim 1, wherein said fluid treatment processor controls said fluid handler in response to said at least one pairing identification code in order to log at least one filtration effect.

15. The fluid filtration security system as recited in claim 1, wherein said fluid treatment processor receives said at least one filter identification code and processes it with said fluid handler identification code and creates said at least one pairing identification code in response thereto.

16. The fluid filtration security system as recited in claim 1 wherein said fluid handler comprises said database or lookup table for storing expiration data or predetermined filter useful life data for any said at least one filter having said usage time that exceeds a predetermined filter useful life, said fluid treatment processor recording an expired filter indicator in said database or lookup table and interrupting or preventing said fluid handler from operating if said fluid treatment processor determines that said at least one filter that is received in said at least one filter receiving area has expired.

17. The fluid filtration security system as recited in claim 12 wherein said fluid treatment processor tracks an actual filter usage time for said at least one filter when it is situated in said at least one filter receiving area and associates said actual filter usage time with at least one of said at least one pairing identification code for said at least one filter or said at least one filter identification code and stores said actual filter usage time in said database or lookup table.

18. The fluid filtration security system as recited in claim 1 wherein said fluid filtration security system generates and maintains said database or lookup table of expired filter identification codes for each of said at least one filter that has an expired useful life, each of said expired filter identification codes being generated when a difference between a usage time of said at least one filter exceeds a predetermined filter maximum running time, said fluid treatment processor interrupting or preventing said fluid handler from operating in response to said expired filter identification code associated with at least one filter that is received or stored in said at least one filter receiving area that has expired.

19. The fluid filtration security system as recited in claim 1 wherein said fluid filtration security system comprises at least one sensor for sensing and logging into said database or lookup table at least one filter usage effectiveness for each of said at least one filter that is received in said at least one filter receiving area, said fluid treatment processor interrupting or preventing said fluid handler from operating if said fluid treatment processor determines that said at least one filter usage effectiveness is below a predetermined threshold.

20. The fluid filtration security system as recited in claim 1 wherein said fluid handler transmits and writes an expiration code onto said at least one filter if said at least one filter is expired, said fluid handler checking for said expiration code for any of said at least one filter that is receiving in said at least one filter receiving area, said fluid treatment processor interrupting or preventing said fluid handler from operating if any of said at least one filter that is inserted into said at least one filter receiving area has expired.

21. The fluid filtration security system as recited in claim 1 wherein each of said at least one filter has an encoded filter maximum running time, said fluid treatment processor interrupting or preventing said fluid handler from operating if a usage time of said at least one filter exceeds said encoded filter maximum running time.

22. The fluid filtration security system as recited in claim 1 wherein said fluid handler is adapted to receive a plurality of the at least one filters, each having a different encoded filter running time or useful life;
said fluid treatment processor enacting expiration timing specific to each of said plurality of filters in response to said encoded filter running time or useful life.

23. The fluid filtration security system as recited in claim 1 wherein said fluid handler comprises said database or lookup table that receives and encodes a unique filter identification code for said at least one filter and pairs said unique filter identification code with filter performance data for said at least one filter, said filter performance data permitting a user to evaluate a performance of said at least one filter, said filter performance data comprising at least one of fluid quality, fluid flow, power draw for said fluid handler, timing or at least one of other system integrity parameters for determining system integrity.

24. The fluid filtration security system as recited in claim 1 wherein said fluid filtration security system comprises communication means for permitting communication between said at least one filter and said fluid handler, said communication means comprising at least one of radio frequency transmission, direct electrical communication, optical signaling, infrared signaling or via a digital network.

25. The fluid filtration security system as recited in claim 1 wherein each of said at least one filter and said fluid handler comprise logic means comprising input, output and memory means.

26. The fluid filtration security system as recited in claim 1 wherein data associated with at least one of said at least one filter or said fluid handler is encrypted before at least one of encoding or transmission.

27. A security method for use in a filtration device for decontaminating or treating air in an environment utilizing the fluid filtration security system of claim 1, said method comprising the following steps:
programming said fluid handler with said fluid handler identification code unique to said fluid handler;
initiating transference of said fluid handler identification code to said at least one filter when said at least one filter is received in said filter receiving area of said fluid handler;
said fluid handler identification code resulting in an exclusive pairing of said at least one filter to said fluid handler, such that said at least one filter cannot be used in any other fluid handler other than said fluid handler which first wrote said fluid handler identification code;
wherein said fluid handler maintains said database or lookup table of said at least one pairing identification code and said at least one filter identification code;
wherein said fluid treatment processor causes said fluid handler identification code that is unique to said fluid handler to be written to said at least one filter using a reader/writer and said fluid treatment processor permanently records said fluid handler identification code into said filter memory of said at least one filter and generates said fluid handler pairing code in response thereto in order to permanently pair said at least one filter to said fluid handler, said reader/writer of said fluid handler being adapted to read said at least one filter identification code that is unique to said at least one filter and said fluid treatment processor stores said at least one filter identification code that is unique to said at least one filter and said at least one pairing code into said database or lookup table in a fluid handler memory associated with said fluid handler;
wherein if said fluid treatment processor determines that said fluid handler identification code for said fluid handler is not either part of said at least one pairing identification code or not permanently written to said filter memory of said at least one filter when said at least one filter is situated in said at least one filter receiving area, then said fluid treatment processor causes said reader/writer to permanently write said fluid handler identification code associated with said fluid handler to said filter memory of said at least one filter and reads said at least one filter identification code and performance data comprising at least one of a maximum filter usage time, preprogrammed lifespan or maximum filter usage code using said reader/writer and causes them to be stored in said database or lookup table into said fluid handler;
wherein said fluid treatment processor reads said fluid handler identification code from said at least one filter when said at least one filter is received in said filter receiving area and verifies that said fluid handler identification code is already resident in said filter memory of said at least one filter or matches said fluid handler identification code stored for that particular said at least one filter in said database and determines whether said fluid handler identification code associated and stored on said at least one filter is the same fluid handler identification code for said fluid handler as originally written to said filter memory when it was inserted into said fluid handler;
wherein if said fluid handler identification code read from said at least one filter is not verified against said database or lookup table, then said fluid treatment processor causes said fluid handler operation to be interrupted and/or prevents said fluid handler from operating, thereby preventing said at least one filter from being used in either said fluid handler or any subsequent fluid handler;
wherein said environment comprises at least one indoor room, said blower in said fluid handler causing at least some contaminated air in said environment to enter into said fluid handler in order to treat said contaminated air;
wherein at least a portion of said contaminated air passes through said at least one filter so that said at least one filter may collect at least some of said contamination when said fluid handler is active and so that said fluid handler may deliver decontaminated or treated air into said environment.

28. A security method for a fluid handler for decontaminating or treating air in an environment utilizing the fluid filtration security system of claim 1, said security method comprising the steps of:
bidirectionally transferring said at least one filter identification code associated with said at least one filter and said fluid handler identification code for said fluid handler to said fluid handler and said at least one filter, respectively, in order to exclusively pair said at least one filter to said fluid handler; and initiating a timer or timing means to clock a filter usage time for said at least one filter after it is received by the fluid handler;

interrupting or preventing the fluid handler from operating if said usage time of said at least one filter exceeds said maximum filter usage time for said at least one filter;

wherein said fluid handler maintains said database or lookup table of said at least one pairing identification code and said at least one filter identification code;

wherein said fluid treatment processor causes said fluid handler identification code that is unique to said fluid handler to be written to said at least one filter using a reader/writer and said fluid treatment processor permanently records said fluid handler identification code into said filter memory of said at least one filter and generates said at least one fluid handler pairing code in response thereto in order to permanently pair said at least one filter to said fluid handler, said reader/writer of said fluid handler being adapted to read said at least one filter identification code that is unique to said at least one filter and said fluid treatment processor stores said at least one filter identification code that is unique to said at least one filter and said at least one pairing code into said database in said fluid handler memory associated with said fluid handler;

wherein if said fluid treatment processor determines that said fluid handler identification code for said fluid handler is not either part of said at least one pairing identification code or not permanently written to said filter memory of said at least one filter when said at least one filter is situated in said at least one filter receiving area, then said fluid treatment processor causes said reader/writer to permanently write said fluid handler identification code associated with said fluid handler to said filter memory of said at least one filter and reads said at least one filter identification code and performance data comprising at least one of a maximum filter usage time, preprogrammed lifespan or maximum filter usage code using said reader/writer and causes them to be stored in said database into said fluid handler;

wherein said fluid treatment processor reads said fluid handler identification code from said at least one filter when said at least one filter is received in said filter receiving area and verifies that said fluid handler identification code is already resident in said filter memory of said at least one filter or matches said fluid handler identification code stored for that particular said at least one filter in said database and determines whether said fluid handler identification code associated and stored on said at least one filter is the same fluid handler identification code for said fluid handler as originally written to said filter memory when it was inserted into said fluid handler;

wherein if said fluid handler identification code read from said at least one filter is not verified against said database or lookup table, then said fluid treatment processor causes operation of said fluid handler to be interrupted and/or prevents said fluid handler from operating, thereby preventing said at least one filter from being used in either said fluid handler or any subsequent fluid handler;

wherein said environment comprises at least one indoor room, said blower in said fluid handler causing at least some contaminated air in said environment to enter into said fluid handler in order to treat said contaminated air;

wherein at least a portion of said contaminated air passes through said at least one filter so that said at least one filter may collect at least some of said contamination when said fluid handler is active and so that said fluid handler may deliver decontaminated or treated air into said environment.

29. The security method for a fluid handler as recited in claim 28 wherein said security method further comprises the steps of:
causing reciprocal communication between said at least one filter and said fluid handler such that said at least one filter receives said fluid handler identification code and said fluid handler receives said filter identification code and a filter time code associated with a predetermined filter time;
subtracting an actual operating time for said at least one filter from said filter time code generally representing an actual time of usage for said at least one filter;
retaining said filter identification code and its associated filter time code in memory, even if said at least one filter is removed and re-installed.

30. The security method for a fluid handler as recited in claim 29 wherein said security method further comprises the step of:
interrupting or ceasing operation of said fluid handler if said actual operating time exceeds the time associated with said filter time code.

31. The security method for a fluid handler as recited in claim 30 wherein said security method further comprises the step of:
annulling said filter time code on said at least one filter if said actual operating time exceeds the time associated with said filter time code and entering said at least one filter identification code into an expired filter database;
checking said filter identification code for any filter inserted into said fluid handler against said expired filter database, and if an annulled filter time code is present in said expired filter database, then preventing said fluid handler from operating.

32. The security method for a fluid handler as recited in claim 29 wherein said security method further comprises the step of:
recording performance data associated with said at least one filter into a performance database having performance data for a plurality of filters;
said performance database comprising filter-specific performance data in association with each of said plurality of filters;
using such performance data to determine a performance and integrity of at least one of said plurality of filters that were used in said fluid handler.

33. A disinfection system for disinfecting fluid in an environment passing through said disinfection system, said disinfection system comprising:
a fluid handler comprising a housing having at least one filter receiving area for receiving at least one filter for filtering air passing through the disinfection system, said fluid handler having a blower that causes air flow in said fluid handler in order to treat the air to facilitate reducing or elimination airborne contaminants, bacteria or pathogens in the air as it passes through said fluid handler;
a filter tracking system adapted to perform at least one of the following: tracking at least one of a filter effectiveness associated with said at least one filter; preventing a re-usage of said at least one filter if said at least one filter fails at least one predetermined filter usage criteria;

preventing use of said at least one filter if a usage time of said at least one filter has expired; or preventing said fluid handler from operating if a verification code associated with said at least one filter is not verified;

wherein said fluid handler maintains a database of said at least one pairing identification code and at least one filter identification code;

wherein a fluid treatment processor causes a fluid handler identification code that is unique to said fluid handler to be written to said at least one filter using a reader/writer and said fluid treatment processor permanently records said fluid handler identification code into a filter memory of said at least one filter and generates at least one fluid handler pairing code in response thereto in order to permanently pair said at least one filter to said fluid handler, said reader/writer of said fluid handler being adapted to read said at least one filter identification code that is unique to said at least one filter and said fluid treatment processor stores said at least one filter identification code that is unique to said at least one filter and said at least one pairing code into said database in a fluid handler memory associated with said fluid handler;

wherein if said fluid treatment processor determines that said fluid handler identification code for said fluid handler is not either part of said at least one pairing identification code or not permanently written to said filter memory of said at least one filter when said at least one filter is situated in said at least one filter receiving area, then said fluid treatment processor causes said reader/writer to permanently write said fluid handler identification code associated with said fluid handler to said filter memory of said at least one filter and reads said at least one filter identification code and performance data comprising at least one of a maximum filter usage time, preprogrammed lifespan or maximum filter usage code using said reader/writer and causes them to be stored in said database into said fluid handler;

wherein said fluid treatment processor reads said fluid handler identification code from said at least one filter when said at least one filter is received in said filter receiving area and verifies that said fluid handler identification code is already resident in said filter memory of said at least one filter or matches said fluid handler identification code stored for that particular said at least one filter in said database and determines whether said fluid handler identification code associated and stored on said at least one filter is the same fluid handler identification code for said fluid handler as originally written to said filter memory when it was inserted into said fluid handler;

wherein if said fluid handler identification code read from said at least one filter is not verified against said database, then said fluid treatment processor causes said fluid handler operation to be interrupted and/or prevents said fluid handler from operating, thereby preventing said at least one filter from being used in either said fluid handler or any subsequent fluid handler;

wherein said environment comprises at least one indoor room, said blower in said fluid handler causing at least some contaminated air in said environment to enter into said fluid handler in order to treat said contaminated air;

wherein at least a portion of said contaminated air passes through said at least one filter so that said at least one filter may collect at least some of said contamination when said fluid handler is active and so that said fluid handler may deliver decontaminated or treated air into said environment.

34. The disinfection system as recited in claim 33 wherein said disinfection system comprises a fluid treatment processor and associated database, said fluid treatment processor causing a fluid handler identification code to be permanently written to said at least one filter when said at least one filter is inserted into said at least one filter receiving area.

35. The disinfection system as recited in claim 34 wherein said at least one filter comprises a filter identification code, said fluid handler comprising said reader/writer is adapted to read said filter identification code for storage in said fluid handler and also for generating a pairing code in response thereto, said pairing code being used to generate said verification code.

36. The disinfection system as recited in claim 35 wherein said pairing code comprises a combination of said fluid handler identification code and said filter identification code;
said fluid treatment processor preventing said fluid handler from operating when said at least one filter is inserted into said fluid handler and said reader/writer reads a code associated with said at least one filter that does not match said pairing code.

37. The disinfection system as recited in claim 34 wherein said at least one filter comprises a filter identification code and a maximum filter time generally representing a maximum time said at least one filter can be used;
said fluid handler comprising said reader/writer is adapted to read said filter identification code and said maximum filter time and record them in a fluid handler memory;
said fluid treatment processor monitoring an actual time of usage for said at least one filter and preventing said fluid handler from operating when said actual time of usage is greater than said maximum filter time.

38. The disinfection system as recited in claim 34 wherein said at least one filter comprises data storage for storing data associated with said at least one filter, said data comprising a maximum filter time, a filter identification code, and a fluid handler identification code.

39. The disinfection system as recited in claim 38 wherein said fluid treatment processor reads said filter identification code when said at least one filter is inserted into said at least one filter receiving area of said fluid handler and combines said filter identification code with said fluid handler identification code to create a pairing code, said fluid treatment processor using said pairing code to control an operation of said fluid handler.

40. The disinfection system as recited in claim 39 wherein said fluid treatment processor prevents said fluid handler from operating if said fluid handler identification code of said pairing code is different from said fluid handler identification code for said fluid handler or if said filter identification code is not verified against said database or lookup table by said fluid treatment processor.

41. A security system for a fluid filtration device for decontaminating or treating air in an environment comprising:
electronic means for transferring data bidirectionally between a changeable filter component and a fluid handler, said fluid handler having a blower that causes air flow in said fluid handler in order to treat the air to facilitate reducing or eliminating airborne contaminants, bacteria or pathogens in the air to facilitate reducing or eliminating airborne contaminants, bacteria or pathogens in the air as it passes through said fluid handler;

at least one of said filter and said fluid handler incorporating preprogrammed unique internal identification codes;

wherein said fluid handler maintains a database or lookup table of said at least one pairing identification code and at least one filter identification code;

wherein a fluid treatment processor causes a fluid handler identification code that is unique to said fluid handler to be written to said at least one filter using a reader/writer and said fluid treatment processor permanently records said fluid handler identification code into a filter memory of said at least one filter and generates said at least one pairing identification code in response thereto in order to permanently pair said at least one filter to said fluid handler, said reader/writer of said fluid handler being adapted to read said at least one filter identification code that is unique to said at least one filter and said fluid treatment processor stores said at least one filter identification code that is unique to said at least one filter and said at least one pairing code into said database in a fluid handler memory associated with said fluid handler;

wherein if said fluid treatment processor determines that said fluid handler identification code for said fluid handler is not either part of said at least one pairing identification code or not permanently written to said filter memory of said at least one filter when said at least one filter is situated in said at least one filter receiving area, then said fluid treatment processor causes said reader/writer to permanently write said fluid handler identification code associated with said fluid handler to said filter memory of said at least one filter and reads said at least one filter identification code and performance data comprising at least one of a maximum filter usage time, preprogrammed lifespan or maximum filter usage code using said reader/writer and causes them to be stored in said database into said fluid handler;

wherein said fluid treatment processor reads said fluid handler identification code from said at least one filter when said at least one filter is received in said filter receiving area and verifies that said fluid handler identification code is already resident in said filter memory of said at least one filter or matches said fluid handler identification code stored for that particular said at least one filter in said database and determines whether said fluid handler identification code associated and stored on said at least one filter is the same fluid handler identification code for said fluid handler as originally written to said filter memory when it was inserted into said fluid handler;

wherein if said fluid handler identification code read from said at least one filter is not verified against said database, then said fluid treatment processor causes said fluid handler operation to be interrupted and/or prevents said fluid handler from operating, thereby preventing said at least one filter from being used in either said fluid handler or any subsequent fluid handler;

wherein said environment comprises at least one indoor room, said blower in said fluid handler causing at least some contaminated air in said environment to enter into said fluid handler in order to treat said contaminated air;

wherein at least a portion of said contaminated air passes through said at least one filter so that said at least one filter may collect at least some of said contamination when said fluid handler is active and so that said fluid handler may deliver decontaminated or treated air into said environment.

42. The security system of claim 41, wherein upon initial installation of said filter to said handler, said fluid handler transfers a handler identification code identifying said handler from said handler to said filter, said filter then recording said handler identification code, said fluid handler further comprising receiving means to receive a filter identification code from said filter, said fluid handler comparing said handler identification code originating in or received by said filter to a filter handler identification code, said security system providing lockout means to prevent said handler from functioning if said handler identification code received from filter does not match its internal handler identification code, thereby preventing the use of an individual filter in more than one handler.

43. The security system of claim 42, wherein upon installation of said filter to said handler and thereafter, initiates timing codes clocking filter usage time, paired or associated with said filter identification code, said security system providing limit means to prevent handler from functioning if a predetermined filter running time has elapsed, said security system further allowing for individual filter removal and re-installation, without loss of timing data.

44. The security system of claim 43, wherein said security system provides limit means to prevent said handler from functioning if a filter usage time has expired, said security system further encoding and retaining said database or lookup table of expired filter identification codes, thus preventing the re-use of an expired filter.

45. The security system of claim 44, wherein all new filters, when installed in said fluid handler communicate a filter identification code to said handler, said handler checking said filter identification code against said database or lookup table of expired codes, said fluid handler preventing operation if a new filter identification code for a new filter is present in said database.

46. The security system of claim 43, wherein said handler transmits, and said filter receives and records, an expiration code upon expiration of said filter, said expiration code being used to prevent said filter from being used in response to said expiration code.

47. The security system of claim 43, wherein said predetermined filter running time is encoded in said filter, said security system allowing for different filter types with varying predetermined filter running times to be received by handler and handler enacting expiration timing specific for said filter type.

48. A security system for a filtration device for decontaminating or treating air in an environment comprising a database which receives and encodes a unique identification code originating in an individual filter and pairs said code with system performance data, said identification code and said performance data allowing a user to evaluate the performance of said individual filter, said performance data consisting of fluid quality, fluid flow, power draw, timing, or other parameters determining system integrity;

wherein a fluid handler maintains said database of said at least one pairing identification code and at least one filter identification code, said fluid handler having a blower that causes air flow in said fluid handler in order to treat the air to facilitate reducing or eliminating airborne contaminants, bacteria or pathogens in the air as it passes through said fluid handler;

wherein a fluid treatment processor causes a fluid handler identification code that is unique to said fluid handler to be written to said individual filter using a reader/writer and said fluid treatment processor permanently records said fluid handler identification code into a filter memory of said at least one filter and generates an at least one fluid handler pairing code in response thereto in order to permanently pair said at least one filter to said fluid handler, said reader/writer of said fluid handler being adapted to read said at least one filter identification code that is unique to said at least one filter and said fluid treatment processor stores said at least one filter identification code that is unique to said at least one filter and said at least one pairing code into said database in a fluid handler memory associated with said fluid handler;

wherein if said fluid treatment processor determines that said fluid handler identification code for said fluid handler is not either part of said at least one pairing identification code or not permanently written to said filter memory of said at least one filter when said at least one filter is situated in at least one filter receiving area, then said fluid treatment processor causes said reader/writer to permanently write said fluid handler identification code associated with said fluid handler to said filter memory of said at least one filter and reads said at least one filter identification code and performance data comprising at least one of a maximum filter usage time, preprogrammed lifespan or maximum filter usage code using said reader/writer and causes them to be stored in said database into said fluid handler;

wherein said fluid treatment processor reads said fluid handler identification code from said at least one filter when said at least one filter is received in said at least one filter receiving area and verifies that said fluid handler identification code is already resident in said filter memory of said at least one filter or matches said fluid handler identification code stored for that particular said at least one filter in said database and determines whether said fluid handler identification code associated and stored on said at least one filter is the same fluid handler identification code for said fluid handler as originally written to said filter memory when it was inserted into said fluid handler;

wherein if said fluid handler identification code read from said at least one filter is not verified against said database, then said fluid treatment processor causes said fluid handler operation to be interrupted and/or prevents said fluid handler from operating, thereby preventing said at least one filter from being used in either said fluid handler or any subsequent fluid handler;

wherein said environment comprises at least one indoor room, said blower in said fluid handler causing at least some contaminated air in said environment to enter into said fluid handler in order to treat said contaminated air;

wherein at least a portion of said contaminated air passes through said at least one filter so that said at least one filter may collect at least some of said contamination when said fluid handler is active and so that said fluid handler may deliver decontaminated or treated air into said environment.

49. The security system of claim 41 wherein communication means between said filter and said handler are via radiofrequency transmission, direct electrical contact, optical signaling, infrared signal, or via digital network.

50. The security system of claim 41 wherein the filter and handler comprise logic means consisting of input, output, and memory means.

51. The security system of claim 41 wherein encoding and/or transmission of handler and/or filter data is encrypted.

52. A method for programming a security system for a filtration device for decontaminating or treating air in an environment utilizing the fluid filtration security system of claim 1, said method comprising the steps of:

programming said fluid handler with said fluid handler identification code unique to said fluid handler;

installing said at least one filter in said fluid handler;

initiating transference of said fluid handler identification code to said at least one filter; and exclusively pairing said at least one filter to said fluid handler such that said at least one filter cannot be used in any other fluid handler than the one to which it was paired;

wherein said fluid handler maintains said database or lookup table of said at least one pairing identification code and said at least one filter identification code;

wherein said fluid treatment processor causes said fluid handler identification code that is unique to said fluid handler to be written to said at least one filter using said reader/writer and said fluid treatment processor permanently records said fluid handler identification code into said filter memory of said at least one filter and generates said at least one pairing identification code in response thereto in order to permanently pair said at least one filter to said fluid handler, said reader/writer of said fluid handler being adapted to read said at least one filter identification code that is unique to said at least one filter and said fluid treatment processor stores said at least one filter identification code that is unique to said at least one filter and said at least one pairing code into said database in said fluid handler memory associated with said fluid handler;

wherein if said fluid treatment processor determines that said fluid handler identification code for said fluid handler is not either part of said at least one pairing identification code or not permanently written to said filter memory of said at least one filter when said at least one filter is situated in said at least one filter receiving area, then said fluid treatment processor causes said reader/writer to permanently write said fluid handler identification code associated with said fluid handler to said filter memory of said at least one filter and reads said at least one filter identification code and performance data comprising at least one of said maximum filter usage time, said preprogrammed lifespan or said maximum filter usage code using said reader/writer and causes them to be stored in said database or lookup table into said fluid handler;

wherein said fluid treatment processor reads said fluid handler identification code from said at least one filter when said at least one filter is received in said filter receiving area and verifies that said fluid handler identification code is already resident in said filter memory of said at least one filter or matches said fluid handler identification code stored for that particular said at least one filter in said database and determines whether said fluid handler identification code associated and stored on said at least one filter is the same fluid handler identification code for said fluid handler as originally written to said filter memory when it was inserted into said fluid handler;

wherein if said fluid handler identification code read from said at least one filter is not verified against said database, then said fluid treatment processor causes said fluid handler operation to be interrupted and/or prevents said fluid handler from operating, thereby preventing said at least one filter from being used in either said fluid handler or any subsequent fluid handler;

wherein said environment comprises at least one indoor room, said blower in said fluid handler causing at least some contaminated air in said environment to enter into said fluid handler in order to treat said contaminated air;

wherein at least a portion of said contaminated air passes through said at least one filter so that said at least one filter may collect at least some of said contamination when said fluid handler is active and so that said fluid handler may deliver decontaminated or treated air into said environment.

53. A method for programming a security system for a filtration device for decontaminating or treating air in an environment utilizing the fluid filtration security system of claim 1, said method comprising the steps of:

installing a fluid filter in a fluid handler;

bidirectionally transferring unique identification codes between said fluid handler and said fluid filter resulting in an exclusive pairing of said fluid filter to said fluid handler; and initiating a timing means to clock the usage time of said fluid filter in said fluid handler by means consisting of magnetic, solid state, cloud, or other equivalent data storage methodologies operating at a local or remote location;

wherein said fluid handler maintains said database or lookup table of said at least one pairing identification code and said at least one filter identification code;

wherein said fluid treatment processor causes said fluid handler identification code that is unique to said fluid handler to be written to said fluid filter using said reader/writer and said fluid treatment processor permanently records said fluid handler identification code into said filter memory of said fluid filter and generates said at least one pairing identification code in response thereto in order to permanently pair said fluid filter to said fluid handler, said reader/writer of said fluid handler being adapted to read said at least one filter identification code that is unique to said fluid filter and said fluid treatment processor stores said at least one filter identification code that is unique to said fluid filter and said at least one pairing code into said database or lookup table in said fluid handler memory associated with said fluid handler;

wherein if said fluid treatment processor determines that said fluid handler identification code for said fluid handler is not either part of said at least one pairing identification code or not permanently written to said filter memory of said fluid filter when said fluid filter is situated in said at least one filter receiving area, then said fluid treatment processor causes said reader/writer to permanently write said fluid handler identification code associated with said fluid handler to said filter memory of said fluid filter and reads said at least one filter identification code and performance data comprising at least one of said maximum filter usage time, said preprogrammed lifespan or said maximum filter usage code using said reader/writer and causes them to be stored in said database or lookup table into said fluid handler;

wherein said fluid treatment processor reads said fluid handler identification code from said fluid filter when said fluid filter is received in said filter receiving area and verifies that said fluid handler identification code is already resident in said filter memory of said fluid filter or matches said fluid handler identification code stored for that particular said fluid filter in said database and determines whether said fluid handler identification code associated and stored on said fluid filter is the same fluid handler identification code for said fluid handler as originally written to said filter memory when it was inserted into said fluid handler;

wherein if said fluid handler identification code read from said fluid filter is not verified against said database or lookup table, then said fluid treatment processor causes said fluid handler operation to be interrupted and/or prevents said fluid handler from operating, thereby preventing said fluid filter from being used in either said fluid handler or any subsequent fluid handler;

wherein said environment comprises at least one indoor room, said blower in said fluid handler causing at least some contaminated air in said environment to enter into said fluid handler in order to treat said contaminated air;

wherein at least a portion of said contaminated air passes through said at least one filter so that said at least one filter may collect at least some of said contamination when said fluid handler is active and so that said fluid handler may deliver decontaminated or treated air into said environment.

* * * * *

UNITED STATES PATENT AND TRADEMARK OFFICE
CERTIFICATE OF CORRECTION

| | |
|---|---|
| PATENT NO. | : 11,406,922 B2 |
| APPLICATION NO. | : 16/419410 |
| DATED | : August 9, 2022 |
| INVENTOR(S) | : David Louis Kirschman |

It is certified that error appears in the above-identified patent and that said Letters Patent is hereby corrected as shown below:

In the Claims

Column 20, Line 35, Claim 1, delete "contaminated" and insert -- contamination -- therefor.

Column 26, Line 62, Claim 33, delete "elimination" and insert -- eliminating -- therefor.

Signed and Sealed this
Seventeenth Day of September, 2024

Katherine Kelly Vidal
*Director of the United States Patent and Trademark Office*